US008143426B2

(12) United States Patent
Condon et al.

(10) Patent No.: US 8,143,426 B2
(45) Date of Patent: *Mar. 27, 2012

(54) IAP INHIBITORS

(75) Inventors: Stephen M. Condon, Glenmoore, PA (US); Matthew G. LaPorte, Honeybrook, PA (US); Yijun Deng, Dresher, PA (US); Susan R. Rippin, Wilmington, DE (US)

(73) Assignee: TetraLogic Pharmaceuticals Corporation, Malvern, PA (US)

(*) Notice: Subject to any disclaimer, the term of this patent is extended or adjusted under 35 U.S.C. 154(b) by 730 days.

This patent is subject to a terminal disclaimer.

(21) Appl. No.: 11/782,315

(22) Filed: Jul. 24, 2007

(65) Prior Publication Data
US 2008/0021066 A1 Jan. 24, 2008

Related U.S. Application Data

(60) Provisional application No. 60/820,141, filed on Jul. 24, 2006.

(51) Int. Cl.
*C07D 209/00* (2006.01)
*C07K 5/06* (2006.01)
(52) U.S. Cl. ... 548/494; 514/18.9; 514/19.3; 514/21.91; 514/415
(58) Field of Classification Search ............. 514/2, 21.9, 514/18.9, 19.3, 21.91, 415; 530/327–331; 548/494
See application file for complete search history.

(56) References Cited

U.S. PATENT DOCUMENTS

| | | | |
|---|---|---|---|
| 3,832,253 A | 8/1974 | DiPalma et al. | |
| 3,854,480 A | 12/1974 | Zaffaroni | |
| 4,278,793 A | 7/1981 | Durckheimer et al. | |
| 4,452,775 A | 6/1984 | Kent | |
| 4,496,658 A * | 1/1985 | Kondo et al. | 435/7.94 |
| 4,525,300 A * | 6/1985 | Yoshida et al. | 530/326 |
| 4,667,014 A | 5/1987 | Nestor, Jr. et al. | |
| 4,748,034 A | 5/1988 | deRham | |
| 4,935,493 A * | 6/1990 | Bachovchin et al. | 530/331 |
| 5,023,077 A * | 6/1991 | Gevas et al. | 424/185.1 |
| 5,075,109 A | 12/1991 | Tice et al. | |
| 5,239,660 A | 8/1993 | Ooi | |
| 5,358,934 A * | 10/1994 | Borovsky et al. | 514/17 |
| 5,468,494 A * | 11/1995 | Gevas et al. | 424/195.11 |
| 5,527,775 A * | 6/1996 | Shorr et al. | 514/12 |
| 5,545,719 A * | 8/1996 | Shashoua | 530/345 |
| 5,578,710 A * | 11/1996 | Ambrosius et al. | 530/412 |
| 5,660,811 A | 8/1997 | Mills | |
| 5,688,506 A * | 11/1997 | Grimes et al. | 424/184.1 |
| 5,766,572 A | 6/1998 | Hasegawa et al. | |
| 5,831,002 A * | 11/1998 | Haupt et al. | 530/329 |
| 6,110,691 A | 8/2000 | Wang et al. | |
| 6,133,437 A | 10/2000 | Korneluk et al. | |
| 6,187,557 B1 | 2/2001 | Rothe et al. | |
| 6,338,835 B1 | 1/2002 | Shochat et al. | |
| 6,608,026 B1 | 8/2003 | Wang et al. | |
| 6,911,426 B2 | 6/2005 | Reed et al. | |
| 6,992,063 B2 | 1/2006 | Shi et al. | |
| 7,217,688 B2 | 5/2007 | Reed et al. | |
| 7,244,851 B2 | 7/2007 | Cohen et al. | |
| 7,309,792 B2 | 12/2007 | Harran et al. | |
| 7,579,320 B2 | 8/2009 | Boudreault et al. | |
| 7,589,118 B2 | 9/2009 | Laurent et al. | |
| 2002/0132786 A1 | 9/2002 | Alnemri et al. | |
| 2002/0160975 A1 | 10/2002 | Alnemri | |
| 2002/0177557 A1 | 11/2002 | Shi | |
| 2004/0054148 A1 | 3/2004 | Alnemri | |
| 2005/0197403 A1 | 9/2005 | Harran et al. | |
| 2005/0234042 A1 | 10/2005 | Palermo et al. | |
| 2005/0261203 A1 | 11/2005 | Cohen et al. | |
| 2006/0014700 A1 | 1/2006 | Cohen et al. | |
| 2006/0025347 A1 | 2/2006 | Condon et al. | |
| 2006/0052311 A1 | 3/2006 | Sharma et al. | |
| 2006/0128632 A1 | 6/2006 | Sharma et al. | |
| 2006/0167066 A1 | 7/2006 | Cohen et al. | |
| 2006/0194741 A1 | 8/2006 | Condon et al. | |
| 2006/0258581 A1 | 11/2006 | Reed et al. | |
| 2006/0264379 A1 | 11/2006 | Jarvis et al. | |
| 2007/0003535 A1 | 1/2007 | Reed et al. | |
| 2007/0042428 A1 | 2/2007 | Springs et al. | |
| 2007/0093428 A1 | 4/2007 | Laurent | |
| 2007/0093429 A1 | 4/2007 | Laurent et al. | |
| 2008/0089896 A1 | 4/2008 | Wang et al. | |
| 2009/0005411 A1 | 1/2009 | Jensen et al. | |
| 2009/0104151 A1 | 4/2009 | Hanson et al. | |
| 2009/0123480 A1 | 5/2009 | Wang et al. | |
| 2009/0142334 A1 | 6/2009 | Korneluk et al. | |
| 2009/0192140 A1 | 7/2009 | Laurent et al. | |
| 2009/0221630 A1 | 9/2009 | Koehler et al. | |
| 2010/0130539 A1 | 5/2010 | Koehler | |

FOREIGN PATENT DOCUMENTS

| | | |
|---|---|---|
| WO | WO 99/15657 A2 | 4/1999 |
| WO | WO 02/16418 A1 | 2/2002 |
| WO | WO 02/26775 A2 | 4/2002 |
| WO | WO 02/30959 A2 | 4/2002 |
| WO | WO 02/096930 A2 | 12/2002 |
| WO | WO 03/018014 A2 | 3/2003 |
| WO | WO 2004/005248 A1 | 1/2004 |
| WO | WO 2004/007529 A2 | 1/2004 |
| WO | WO 2004/072105 A2 | 8/2004 |

(Continued)

OTHER PUBLICATIONS

Kohli et al., SMAC/Diablo-dependent apoptosis induced by nonsteroidal nti-inflammatory drugs (NSAIDs) in colon cancer cells, 2004, PNAS 101(48):16897-16902. Ripka et al., Peptidomimetic design, 1998, Curr. Op. Chem. Biol. 2:441-452.

Hruby et al., Synthesis of oligopeptide and peptidomimetic libraries, 1997, Curr. Op. in Chem. Biol. 1:114-119.

Hruby et al., Conformational and Topographical Considerations in Designing Agonist Peptidomimetics from Peptide Leads, 2000, Curr. Med. Chem. 7(9):945-970.

Nikolovska-Coleska et al., Development and optimization of a binding assay for the XIAP BIR3 domain using fluorescence polarization, 2004, Anal. Biochem. 332:261-273.

Macor et al., The Synthesis of a Conformationally Restricted Analog of the Anti-Migraine Drug Sumatriptan, 1992, Tetrahedron Lett. 33(52):8011-8014.

(Continued)

*Primary Examiner* — David Lukton
(74) *Attorney, Agent, or Firm* — Banner & Witcoff, Ltd.

(57) ABSTRACT

Smac mimetics that inhibit IAPs.

42 Claims, No Drawings

FOREIGN PATENT DOCUMENTS

| | | |
|---|---|---|
| WO | WO 2005/069888 A2 | 8/2005 |
| WO | WO 2005/069894 A2 | 8/2005 |
| WO | WO 2005/078989 A2 | 8/2005 |
| WO | WO 2005074989 | 8/2005 |
| WO | WO 2005/084317 A2 | 9/2005 |
| WO | WO 2005/094818 A1 | 10/2005 |
| WO | WO 2005/097791 A1 | 10/2005 |
| WO | WO 2006/010118 A2 | 1/2006 |
| WO | WO 2006/014361 A1 | 2/2006 |
| WO | WO 2006/017295 A2 | 2/2006 |
| WO | WO 2006/020060 A2 | 2/2006 |
| WO | WO 2006/069063 A1 | 6/2006 |
| WO | WO 2006/091972 A2 | 8/2006 |
| WO | WO 2006/122408 A1 | 11/2006 |
| WO | WO 2006/128455 A2 | 12/2006 |
| WO | WO 2006/133147 A2 | 12/2006 |
| WO | WO 2007/021825 | 2/2007 |
| WO | WO 2007/101347 A1 | 9/2007 |
| WO | WO 2007/106192 A2 | 9/2007 |
| WO | WO 2007101347 | 9/2007 |
| WO | WO 2007/130626 A2 | 11/2007 |
| WO | WO 2007/136921 | 11/2007 |
| WO | WO 2008/016893 | 2/2008 |
| WO | WO 2008057172 | 5/2008 |
| WO | WO 2008134679 | 11/2008 |

OTHER PUBLICATIONS

Hansen et al., Re-examination and further development of a precise and rapid dye method for measuring cell growth/cell kill, 1989, J. Immunol. Methods 119:203-210.
Chawla-Sarkar, Preferential Induction of Apoptosis by Interferon (IFN)-β Compared with IFN-α2: Correlation with TRAIL/Apo2L Induction in Melanoma Cell Lines, 2001, Clin. Can. Res. 7:1821-1831.
Sun et al., Structure-based Design of Potent, Conformationally Constrained Smac Mimetics, 2004, J. Am. Chem. Soc. 126:16686-16687.
Park et al., Non-peptide small molecule inhibitors of XIAP, 2004, Bioorganic & Med. Chem. Lett. 15:771-775.
Lang's Handbook of Chemistry, Dean ed., Table 7-2, 1985.
Ambrosini et al., Induction of Apoptosis and Inhibition of Cell Proliferation by urviving Gene Targeting, 1998, J. Biol. Chem. 273(18):11177-11182.
Chai et al., Structural and biochemical basis of apoptotic activation by Smac/DIABLO, 2000, Nature 406:855-862.
Zuckerman et al., Efficient Method for the Preparation of Peptoids [Oligo(N-substituted glycines)] by Submonomer Solid-Phase Synthesis, 1992, J. Am. Chem. Soc. 114:10646-10647.
Weinstein ed., Chemistry and Biochemistry of Amino Acids, Peptides, and Proteins, 1983, Marcel Dekker, Inc., New York, New York (TOC).
Wyllie et al., Cell Death: the significance of apoptosis, 1980, Int. Rev. Cytol. 68:251-306.
Wyllie, Glucocorticoid-induced thymocyte apoptosis is associated with endogenous endonuclease activation, 1981, Nature 284:555-556.
Fulda et al., Smac agonists sensitize for Apo2L/TRAIL-or anticancer drug-induced apoptosis and induce regression of malignant glioma in vivo, 2002, Nat. Med. 8(8):808-815.
Deveraux et al., IAP family proteins-suppressors of apoptosis, 1999, Genes & Devel. 13:239-252.
Kasof et al., Livin, a Novel Inhibitor of Apoptosis Protein Family Member, 2001, J. Biol. Chem. 276(5):3238-3246.
Vucic et al., ML-IAP, a novel inhibitor of apoptosis that is preferentially expressed in human melanomas, 2000, Curr. Biol. 10:1359-1366.
Ashhab et al., two splicing variants of a new inhibitor of apoptosis gene with different biological properties and tissue distribution pattern, 2001, FEBS Lett. 495:56-60.
Du et al., Smac, a mitochondrial Protein that Promotes Cytochrome c-Dependent Caspase Activation by Eliminating IAP Inhibitiion, 2000, Cell 102:33-42.
Verhagen et al., Identification of DIABLO, a Mammalian Protein that Promotes Apoptosis by Binding to and Antagonizing IAP Proteins, 2000, Cell 102:43-53.
Hay, Understanding IAP function and regulation: a view from Drosophila, 2000, Cell Death and Diff. 7:1045-1056.
Chan et al., Fmoc Solid Phase Peptide Synthesis: A Practical Approach, 2000, Oxford University Press (TOC).
Boxrud et al., Streptokinase Binds to Human Plasmin with High Affinity, Perturbs the Plasmin Active Site, and Induces Expression of a Substrate Recognition Exosite for Plasminogen, 2000, J. Biol. Chem. 275(19):14579-14589.
Owenius et al., Properties of Spin and Fluorescent Labels at a Receptor-Ligand Interface, 1999, Biophys. J. 77:2237-2250.
Hiratsuka, ATP-induced Opposite Changes in the Local Environments around $Cys^{697}(SH2)$ and $Cys^{707}(SH1)$ of the Myosin Motor Domain Reveled by the Prodan Fluorescence, 1999, J. Biol. Chem. 274(41):29156-29163.
Wu et al., Structural basis of IAP recognition by Smac/DIABLO, 2000, Nature 408:1008-1012.
Chen et al., Grim, a novel cell death gene in drospohila, 1996, Genes & Devel. 10:1773-1782.
Goyal et al., Induction of apoptosis by drosophila reaper, hid and grim through inhibition of IAP function, 2000, EMBO J. 19(4):589-597.
Jones et al., Improved methods for building protein models in electron density maps and thelocation of errors in these models, 1991, Acta Crystallogr. A47:110-119.
Kraulis, Molscript: a program to produce both detailed and schematic plots of protein structures, 1991, J. Appl. Crystallogr. 24:946-950.
Lisi et al., Diverse Domains of THREAD/DIAPI are Required to Inhibit Apoptosis Induced by Reaper and HID in Drosophila, 1999, Genetics Soc. Am. 154:669-678.
Liu, Structural basis for binding of Smac/DIABLO to the XIAP BIR3 domain, Dec. 2000, Nature, pp. 1004-1008.
McCarthy et al., Apoptosis induced by drosophila reaper and grim in a human system, 1999, J. Biol. Chem. 273(37):24009-24015.
Morgan et al., Approaches to the Discovery of Non-Peptide Ligands for Peptide Receptors and Peptidases. 1989, Ann. Rep. Med. Chem. 243-252.
Navaza, AmoRe: an Automated Package for Molecular Replacement, 1994, Acta Cryst. A50:157-163.
Nicholls et al., Protein folding and association: insights from the interfacial and thermodynamic properties of hydrocarbons, 1991, Proteins: Struct. Funct. & Genet. 11:281-296.
Srinivasula et al., A conserved XIAP-interaction motif in caspase-9 and Smac/DIABLO regulates caspase activity and apoptosis, 2001, Nature 410:112-116.
Sun et al., NMR Structure and Mutagenesis of the Third Bir Domain of the Inhibitor of Apoptosis Protein XIAP, 2000, J. Biol. Chem. 275(43):33777-33781.
Terwilliger et al., The CCP4 suite: Programs for protein crystallography, 1994, Acta Crystallogr. D50:760-763.
Terwilliger et al., Correlated Phasing of Multiple Isomorphous Replacement Data, 1996, Acta Crystallogr. D52:749-757.
Vucic et al., Inhibition of Reaper-induced apoptosis by interaction with inhibitor of apoptosis proteins (IAPS), 1997, Proc. Natl. Acad. Sci. USA 94:10183-10188.
Stellar, Mechanisms and Genes of Cellular Suicide, 1995, Science 267:1445-1449.
Jacobson et al., Programmed Cell Death in Animal Development, 1997, Cell 88:347-354.
Hengartner, Programmed cell death in invertebrates, 1996, Curr. Opin. Genet. Dev. 6:34-38.
Horvitz, Genetic Control of Programmed Cell Death in the Nematode *Caenorhabditis elegans*, 1999, Can. Res. 59:1701s-1706s.
Miller, An exegesis of IAPs: salvation and surprises from BIR motifs, 1999, Cell Biol. 9:323-328.
Deveraux et al., Cleavage of human inhibitor of apoptosis protein XIAP results in fragments with distinct specificities for caspases, 1999, EMBO J. 18(19):5242-5251.
Takahashi et al., A Single BIR Domain XIAP Sufficient for Inhibiting Caspases, 1998, J. Biol. Chem. 273(14):7787-7790.
Sun et al., NMR structure and mutagenesis of the inhibitor-of-apoptosis protein XIAP, 1999, Nature 40:818-822.
Shi, Survivin structure: crystal unclear, 2000, Nat. Str. Biol. 7(8):620-623.

Verdecia et al., Structure of the human anti-apoptotic protein surviving reveals a dimeric arrangement, 2000, Nat. Struc. Biol. 7(7):602-608.

Chantalat et al., Crystal Structure of Human Survivin Reveals a Bow Tie-Shaped Dimer with Two Unusual α-Helical Extensions, 2000, Mol. Cell. 6:183-189.

Wang et al., The Drosphila Caspase Inhibitor DIAP1 is Essential for Cell Survival and Is Negatively Regulated by HID, 1999, Cell 98:453-463.

Hirel et al., Extent of N-terminal methionine excision from *Escherichia coli* proteins is governed by the side-chain length of the penultimate amino acid, 1989, Proc. Natl. Acad. Sci. USA 86:8247-8251.

Freidinger et al., Synthesis of 9pflourenylmethyloxycarbobyl-protected n-alkyl amino acids by reductin of oxazolidinones, 1983, J. Org. Chem. 48:77-81.

Srinivasula et al., Molecular Determinants of the Caspase-promoting activity of Smac/DIABLO and its role in the death receptor pathway, 2000, J. Biol. Chem. 275(46):36152-36157.

Wu et al., Structural Analysis of a Functional DIAP1 Fragment Bound to Grim and Hid Peptides, 2001, Mol. Cell 8:95-104.

Oost et al., Discovery of Potent Antagonists of the Antiapoptotic Protein XIAP for the Treatment of Cancer, 2004, J. Med. Chem. 47:4417-4426.

Vucic et al., Engineering ML-IAP to produce an extraordinarily potent caspase 9 inhibitor: implications for Smac-dependent anti-apoptotic activity of ML-IAP, 2005, Biochem. J. 385(1):11-20.

International Search Report and Writtem Opinion of ISA for PCT/US2007/074225 . . . , Jan. 25, 2008.

International Search Report and Written Opinion of ISA for PCT/US2007/074209 . . . , Jan. 28, 2008.

Bockbrader et al., "A small molecule Smac-mimic compound induces apoptosis and sensitizes TRAIL—and etoposide-induced apoptosis in breast cancer cells," Oncogene, 2005, vol. 24, No. 49, pp. 7381-7388.

Fotin-Mleczek et al., "Cationic cell-penetrating peptides interfere with TNF signalling by induction of TNF receptor internalization," Journal of Cell Science, 2005, vol. 118, No. 15, pp. 3339-3351.

Li et al., "A Small Molecule Smac Mimic Potentiates TRAIL—and TNF-α-Mediated Cell Death," Science, 2004, vol. 305, No. 5689, pp. 1471-1474.

\* cited by examiner

IAP INHIBITORS

This application claims priority to and benefit of U.S. Provisional Application No. 60/820,141 entitled "IAP Inhibitors" filed on Jul. 24, 2006; the entire contents of which is hereby incorporated by reference in its entirety.

Apoptosis (programmed cell death) plays a central role in the development and homeostasis of all multi-cellular organisms. Apoptosis can be initiated within a cell from an external factor such as a chemokine (an extrinsic pathway) or via an intracellular event such a DNA damage (an intrinsic pathway). Alterations in apoptotic pathways have been implicated in many types of human pathologies, including developmental disorders, cancer, autoimmune diseases, as well as neurodegenerative disorders. One mode of action of chemotherapeutic drugs is cell death via apoptosis.

Apoptosis is conserved across species and executed primarily by activated caspases, a family of cysteine proteases with aspartate specificity in their substrates. These cysteine containing aspartate specific proteases ("caspases") are produced in cells as catalytically inactive zymogens and are proteolytically processed to become active proteases during apoptosis. Once activated, effector caspases are responsible for proteolytic cleavage of a broad spectrum of cellular targets that ultimately lead to cell death. In normal surviving cells that have not received an apoptotic stimulus, most caspases remain inactive. If caspases are aberrantly activated, their proteolytic activity can be inhibited by a family of evolutionarily conserved proteins called IAPs (inhibitors of apoptosis proteins).

The IAP family of proteins suppresses apoptosis by preventing the activation of procaspases and inhibiting the enzymatic activity of mature caspases. Several distinct mammalian IAPs including XIAP, c-IAP1, c-IAP2, ML-IAP, NAIP (neuronal apoptosis inhibiting protein), Bruce, and survivin, have been identified, and they all exhibit anti-apoptotic activity in cell culture. IAPs were originally discovered in baculovirus by their functional ability to substitute for P35 protein, an anti-apoptotic gene. IAPs have been described in organisms ranging from Drosophila to human, and are known to be overexpressed in many human cancers. Generally speaking, IAPs comprise one to three Baculovirus IAP repeat (BIR) domains, and most of them also possess a carboxyl-terminal RING finger motif. The BIR domain itself is a zinc binding domain of about 70 residues comprising 4 alpha-helices and 3 beta strands, with cysteine and histidine residues that coordinate the zinc ion. It is the BIR domain that is believed to cause the anti-apoptotic effect by inhibiting the caspases and thus inhibiting apoptosis. XIAP is expressed ubiquitously in most adult and fetal tissues. Overexpression of XIAP in tumor cells has been demonstrated to confer protection against a variety of pro-apoptotic stimuli and promotes resistance to chemotherapy. Consistent with this, a strong correlation between XIAP protein levels and survival has been demonstrated for patients with acute myelogenous leukemia. Down-regulation of XIAP expression by antisense oligonucleotides has been shown to sensitize tumor cells to death induced by a wide range of pro-apoptotic agents, both in vitro and in vivo. Smac/DIABLO-derived peptides have also been demonstrated to sensitize a number of different tumor cell lines to apoptosis induced by a variety of pro-apoptotic drugs.

In normal cells signaled to undergo apoptosis, however, the IAP-mediated inhibitory effect must be removed, a process at least in part performed by a mitochondrial protein named Smac (second mitochondrial activator of caspases). Smac (or, DIABLO), is synthesized as a precursor molecule of 239 amino acids; the N-terminal 55 residues serve as the mitochondria targeting sequence that is removed after import. The mature form of Smac contains 184 amino acids and behaves as an oligomer in solution. Smac and various fragments thereof have been proposed for use as targets for identification of therapeutic agents.

Smac is synthesized in the cytoplasm with an N-terminal mitochondrial targeting sequence that is proteolytically removed during maturation to the mature polypeptide and is then targeted to the inter-membrane space of mitochondria. At the time of apoptosis induction, Smac is released from mitochondria into the cytosol, together with cytochrome c, where it binds to IAPs, and enables caspase activation, therein eliminating the inhibitory effect of IAPs on apoptosis, Whereas cytochrome c induces multimerization of Apaf-1 to activate procaspase-9 and -3, Smac eliminates the inhibitory effect of multiple IAPs. Smac interacts with essentially all IAPs that have been examined to date including XIAP, c-IAP1, c-IAP2, ML-IAP, and survivin. Thus, Smac appears to be a master regulator of apoptosis in mammals.

It has been shown that Smac promotes not only the proteolytic activation of procaspases, but also the enzymatic activity of mature caspase, both of which depend upon its ability to interact physically with IAPs. X-ray crystallography has shown that the first four amino acids (AVPI) of mature Smac bind to a portion of IAPs. This N-terminal sequence is essential for binding IAPs and blocking their anti-apoptotic effects.

Current trends in cancer drug design focus on selective targeting to activate the apoptotic signaling pathways within tumors while sparing normal cells. The tumor specific properties of specific chemotherapeutic agents, such as TRAIL have been reported. The tumor necrosis factor-related apoptosis-inducing ligand (TRAIL) is one of several members of the tumor necrosis factor (TNF) superfamily that induce apoptosis through the engagement of death receptors. TRAIL interacts with an unusually complex receptor system, which in humans comprises two death receptors and three decoy receptors. TRAIL has been used as an anti-cancer agent alone and in combination with other agents including ionizing radiation. TRAIL can initiate apoptosis in cells that overexpress the survival factors Bcl-2 and Bcl-XL, and may represent a treatment strategy for tumors that have acquired resistance to chemotherapeutic drugs. TRAIL binds its cognate receptors and activates the caspase cascade utilizing adapter molecules such as TRADD. TRAIL signaling can be inhibited by overexpression of cIAP-1 or 2, indicating an important role for these proteins in the signaling pathway. Currently, five TRAIL receptors have been identified. Two receptors TRAIL-R1 (DR4) and TRAIL-R2 (DR5) mediate apoptotic signaling, and three non-functional receptors, DcR1, DcR2, and osteoprotegerin (OPG) may act as decoy receptors. Agents that increase expression of DR4 and DR5 may exhibit synergistic anti-tumor activity when combined with TRAIL.

The basic biology of how IAP antagonists work suggests that they may complement or synergize other chemotherapeutic/anti-neoplastic agents and/or radiation. Chemotherapeutic/anti-neoplastic agents and radiation would be expected to induce apoptosis as a result of DNA damage and/or the disruption of cellular metabolism.

Inhibition of the ability of a cancer cell to replicate and/or repair DNA damage will enhance nuclear DNA fragmentation and thus will promote the cell to enter the apoptotic pathway. Topoisomerases, a class of enzymes that reduce supercoiling in DNA by breaking and rejoining one or both strands of the DNA molecule, are vital to cellular processes, such as DNA replication and repair. Inhibition of this class of enzymes impairs the cells ability to replicate as well as to repair damaged DNA and activates the intrinsic apoptotic pathway.

The main pathways leading from topoisomerase-mediated DNA damage to cell death involve activation of caspases in the cytoplasm by proapoptotic molecules released from mitochondria, such as Smac. The engagement of these apoptotic effector pathways is tightly controlled by upstream regulatory pathways that respond to DNA lesions-induced by topoisomerase inhibitors in cells undergoing apoptosis. Initiation of cellular responses to DNA lesions-induced by topoisomerase inhibitors is ensured by the protein kinases which bind to DNA breaks. These kinases (non-limiting examples of which include Akt, JNK and P38) commonly called "DNA sensors" mediate DNA repair, cell cycle arrest and/or apoptosis by phosphorylating a large number of substrates, including several downstream kinases.

Platinum chemotherapy drugs belong to a general group of DNA modifying agents. DNA modifying agents may be any highly reactive chemical compound that bonds with various nucleophilic groups in nucleic acids and proteins and cause mutagenic, carcinogenic, or cytotoxic effects. DNA modifying agents work by different mechanisms, disruption of DNA function and cell death; DNA damage/the formation of cross-bridges or bonds between atoms in the DNA; and induction of mispairing of the nucleotides leading to mutations, to achieve the same end result. Three non-limiting examples of a platinum containing DNA modifying agents are cisplatin, carboplatin and oxaliplatin.

Cisplatin is believed to kill cancer cells by binding to DNA and interfering with its repair mechanism, eventually leading to cell death. Carboplatin and oxaliplatin are cisplatin derivatives that share the same mechanism of action. Highly reactive platinum complexes are formed intracellularly and inhibit DNA synthesis by covalently binding DNA molecules to form intrastrand and interstrand DNA crosslinks.

Non-steroidal anti-inflammatory drugs (NSAIDs) have been shown to induce apoptosis in colorectal cells. NSAIDs appear to induce apoptosis via the release of Smac from the mitochondria (PNAS, Nov. 30, 2004, vol. 101:16897-16902). Therefore, the use of NSAIDs in combination with Smac mimetics would be expected to increase the activity each drug over the activity of either drug independently.

Many naturally occurring compounds isolated from bacterial, plant, and animals can display potent and selective biological activity in humans including anticancer and antineoplastic activities. In fact, many natural products, or semi-synthetic derivatives thereof, which possess anticancer activity, are already commonly used as therapeutic agents; these include paclitaxel, etoposide, vincristine, and camptothecin amongst others. Additionally, there are many other classes of natural products such as the indolocarbazoles and epothilones that are undergoing clinical evaluation as anticancer agents.

A reoccurring structural motif in many natural products is the attachment of one or more sugar residues onto an aglycone core structure. In some instances, the sugar portion of the natural product is critical for making discrete protein-ligand interactions at its site of action (i.e., pharmacodynamics) and removal of the sugar residue results in significant reductions in biological activity. In other cases, the sugar moiety or moieties are important for modulating the physical and pharmacokinetic properties of the molecule. Rebeccamycin and staurosporine are representative of the sugar-linked indolocarbazole family of anticancer natural products with demonstrated anti-kinase and anti-topoisomerase activity.

SUMMARY OF THE INVENTION

The present invention provides IAP antagonists that are peptidomimetic compounds that mimic the tertiary binding structure and activity of the N-terminal four amino acids of mature Smac to IAPs. The invention also provides methods of using these mimetics to modulate apoptosis and further for therapeutic purposes.

One aspect of the present invention is an antagonist/inhibitor of an IAP that is a peptidomimetic compound that mimics the tertiary binding structure of the N-terminal amino acids of mature Smac to IAPs and that has either an optionally-substituted 5-, 6-, or 7-membered heterocycloalkyl group with at least one N or O atom in the ring, such as, for example, D- or L-fucose, xylose, galactose, glucose, pyrrolidine, piperidine, or perhydroazapine, or an optionally-substituted heteroaryl group containing at least one N atom such as, for example, pyridine, pyrimidine, or pyrazine, at the C-terminus of the peptidomimetic. Such compounds include but are not limited to monomers, homodimers, and heterodimers of such Smac mimetics.

In one aspect of the present invention, an IAP antagonist that is a monomeric, homodimeric or heterodimeric compound having the general formula I or IV, depicted below, and pharmaceutically acceptable salts thereof. Solvates including hydrates, stereoisomers including enantiomers, crystalline forms including polymorphs, and the like are encompassed within the scope of the invention.

Another embodiment of the present invention is the therapeutic combination of compounds of the present invention with TRAIL or other chemical or biological agents which bind to and activate the TRAIL receptor(s) TRAIL has received considerable attention recently because of the finding that many cancer cell types are sensitive to TRAIL-induced apoptosis, while most normal cells appear to be resistant to this action of TRAIL. TRAIL-resistant cells may arise by a variety of different mechanisms including loss of the receptor, presence of decoy receptors, or overexpression of FLIP which competes for zymogen caspase-8 binding during DISC formation. In TRAIL resistance, Smac mimetics increase tumor cell sensitivity to TRAIL leading to enhanced cell death, the clinical correlations of which are expected to be increased apoptotic activity in TRAIL resistant tumors, improved clinical response, increased response duration, and ultimately, enhanced patient survival rate. In support of this, reduction in XIAP levels by in vitro antisense treatment has been shown to cause sensitization of resistant melanoma cells and renal carcinoma cells to TRAIL (Chawla-Sarkar, et al., 2004). The Smac mimetics disclosed herein bind to IAPs and inhibit their interaction with caspases, therein potentiating TRAIL-induced apoptosis.

Another embodiment of the present invention provides Smac mimetics which act synergistically with topoisomerase inhibitors to potentiate their apoptotic inducing effect. Topoisomerase inhibitors inhibit DNA replication and repair, thereby promoting apoptosis and have been used as chemo-thermotherapeutic agents. Topoisomerase inhibitors promote DNA damage by inhibiting the enzymes that are required in the DNA repair process. Therefore, export of Smac from the mitochondria into the cell cytosol is provoked by the DNA damage caused by topoisomerase inhibitors.

Topoisomerase inhibitors of both the Type I class (camptothecin, topotecan, SN-38 (irinotecan active metabolite) and the Type II class (etoposide) show potent synergy with the Smac mimetics of the invention in a multi-resistant glioblastoma cell line (T98G), breast cancer line (MDA-MB-231), and ovarian cancer line (OVCAR-3) among others. Further examples of topoisomerase inhibiting agents that may be used include, but are not limited to, irinotecan, topotecan, etoposide, amsacrine, exatecan, gimatecan, etc. Other topoisomerase inhibitors include, for example, Aclacinomycin A, camptothecin, daunorubicin, doxorubicin, ellipticine, epirubicin, and mitaxantrone.

In another embodiment of the invention, the chemotherapeutic/anti-neoplastic agent may be a platinum containing compound. In one embodiment of the invention the platinum containing compound is cisplatin. Cisplatin can synergize with a Smac peptidomimetic and potentiate the inhibition of an IAP, such as but not limited to XIAP, cIAP-1, c-IAP-2, ML-IAP, etc. In another embodiment a platinum containing compound is carboplatin. Carboplatin can synergize with a Smac peptidomimetic and potentiate the inhibition of an IAP, including, but not limited to, XIAP, cIAP-1, c-IAP-2, ML-TAP, etc. In another embodiment a platinum containing compound is oxaliplatin. The oxaliplatin can synergize with a Smac peptidomimetic and potentiate the inhibition of an TAP, including, but not limited to, XIAP, cIAP-1, c-IAP-2, ML-IAP, etc.

In another embodiment of the invention, the chemotherapeutic/anti-neoplastic agent that synergizes with a compound according to the present invention is a taxane. Taxanes are anti-mitotic, mitotic inhibitors or microtubule polymerization agents. Taxanes include but are not limited to, docetaxel and paclitaxel.

Taxanes are characterized as compounds that promote assembly of microtubules by inhibiting tubulin depolymerization, thereby blocking cell cycle progression through centrosomal impairment, induction of abnormal spindles and suppression of spindle microtubule dynamics. The unique mechanism of action of taxane is in contrast to other microtubule poisons, such as Vinca alkaloids, colchicine, and cryptophycines, which inhibit tubulin polymerization. Microtubules are highly dynamic cellular polymers made of alpha-beta-tubulin and associated proteins that play key roles during mitosis by participating in the organization and function of the spindle, assuring the integrity of the segregated DNA. Therefore, they represent an effective target for cancer therapy.

In another embodiment, any agent that activates the intrinsic apoptotic pathway and/or causes the release of Smac or cytochrome c from the mitochondria has the potential to act synergistically with a Smac mimetic.

A combination of a Smac peptidomimetic and a chemotherapeutic/anti neoplastic agent and/or radiation therapy of any type that activates the intrinsic pathway may provide a more effective approach to destroying tumor cells. Smac peptidomimetics interact with IAP's, such as XIAP, cIAP-1, cIAP-2, ML-IAP, etc., and block the IAP mediated inhibition of apoptosis while chemotherapeutics/anti neoplastic agents and/or radiation therapy kills actively dividing cells by activating the intrinsic apoptotic pathway leading to apoptosis and cell death. As is described in more detail below, embodiments of the invention provide combinations of a Smac pepidomimetc and a chemotherapeutic/anti-neoplastic agent and/ or radiation which provide a synergistic action against unwanted cell proliferation. This synergistic action between a Smac peptidomimetic and a chemotherapeutic/anti-neoplastic agent and/or radiation therapy can improve the efficiency of the chemotherapeutic/anti-neoplastic agent and/or radiation therapy. This will allow for an increase in the effectiveness of current chemotherapeutic/anti-neoplastic agents or radiation treatment allowing the dose of the chemotherapeutic/anti-neoplastic agent to be lowered, therein providing both a more effective dosing schedule as well as a more tolerable dose of chemotherapeutic/anti-neoplastic agent and/or radiation therapy.

For simplicity and illustrative purposes, the principles of the invention are described by referring mainly to specific illustrative embodiments thereof. In addition, in the following description, numerous specific details are set forth in order to provide a thorough understanding of the invention. It will be apparent however, to one of ordinary skill in the art, that the invention may be practiced without limitation to these specific details. In other instances, well known methods and structures have not been described in detail so as not to unnecessarily obscure the invention.

DEFINITIONS

"Alkyl" and "alkylene" mean a branched or unbranched, saturated or unsaturated (i.e. alkenyl, alkenylene, alkynyl, alkynylene) non-cyclic aliphatic hydrocarbon group, having up to 12 carbon atoms unless otherwise specified. (However, if alkenylene is specified but alkynylene is not, then alkynylene is excluded, E.g., "alkylene or alkenylene" excludes alkynylene.) When used as part of another term, for example, "alkylamino", the alkyl portion may be a saturated hydrocarbon chain, however also includes unsaturated hydrocarbon carbon chains such as "alkenylamino" and "alkynylamino". Examples of particular alkyl groups include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl", "$C_1$-$C_4$ alkyl" and "alkyl of 1 to 4 carbon atoms" are synonymous and used interchangeably to mean methyl, ethyl, 1-propyl, isopropyl, cyclopropyl, 1-butyl, sec-butyl or t-butyl. Unless specified, optionally substituted alkyl groups may contain one, two, three or four substituents which may be the same or different. Examples of the above substituted alkyl groups include, but are not limited to; cyanomethyl, nitromethyl, hydroxymethyl, trityloxymethyl, propionyloxymethyl, aminomethyl, carboxymethyl, carboxyethyl, carboxypropyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-amino(iso-propyl), 2-carbamoyloxyethyl and the like. The alkyl group may also be substituted with a carbocycle group. Examples include cyclopropylmethyl, cyclobutylmethyl, cyclopentylmethyl, and cyclohexylmethyl groups, as well as the corresponding-ethyl, -propyl, -butyl, -pentyl, -hexyl groups, etc. Particular substituted alkyls are substituted methyl groups. Examples of the substituted methyl groups include groups such as hydroxymethyl, protected hydroxymethyl (e.g., tetrahydropyranyloxymethyl), acetoxymethyl, carbamoyloxymethyl, trifluoromethyl, chloromethyl, carboxymethyl, bromomethyl and iodomethyl. "Cycloalkyl" means a saturated or unsaturated cyclic aliphatic hydrocarbon group, having up to 12 carbon atoms unless otherwise specified and includes cyclic and polycyclic, including fused cycloalkyl.

"Amino" denotes primary (i.e., —$NH_2$), secondary (i.e., —NRH) and tertiary (i.e. —NRR) amines.

Particular secondary and tertiary amines are alkylamine, dialkylamine, arylamine, diarylamine, aralkylamine and diaralkylamine. Particular secondary and tertiary amines are methylamine, ethylamine, propylamine, isopropylamine, phenylamine, benzylamine dimethylamine, diethylamine, dipropylamine and disopropylamine.

"Aryl" when used alone or as part of another term means a carbocyclic aromatic group whether or not fused having the number of carbon atoms designated or if no number is designated, up to 14 carbon atoms Particular aryl groups include phenyl, naphthyl, biphenyl, phenanthrenyl, naphthacenyl, and the like (see e.g. Lang's Handbook of Chemistry (Dean, J. A., ed) 13$^{th}$ ed. Table 7-2 [1985]). In a particular embodiment an aryl group is phenyl. Optionally substituted phenyl or optionally substituted aryl denotes a phenyl group or aryl group that may be substituted with one, two, three, four or five substituents chosen, unless otherwise specified, from halogen (F, Cl, Br, I), hydroxy, protected hydroxy, cyano, nitro, alkyl (such as $C_1$-$C_6$ alkyl), alkoxy (such as $C_1$-$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, arylsulfonylamino, heterocyclylsulfonylamino, heterocyclyl, aryl, or other groups specified. One or more methyne (CH) and/or methylene ($CH_2$) groups in these substituents may in turn be substituted with a similar group as those denoted above. Examples of the term "substituted phenyl" includes but is not limited to a mono- or di(halo)phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4 ethylphenyl, 3-(n-propyl)phenyl and the like; a mono or di(alkoxy) phenyl group, for example, 3,4-dimethoxyphenyl, 3-methoxy-4-benzyloxyphenyl, 3-methoxy-4-(1-chloromethyl)benzyloxy-phenyl, 3-ethoxyphenyl, 4-(isopropoxy) phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl; a mono- or di(hydroxymethyl)phenyl or (protected hydroxymethyl)phenyl such as 3-(protected hydroxymethyl) phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino. Particular substituted phenyl groups are 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl) benzyloxy-6-methyl sulfonyl aminophenyl groups. Fused aryl rings may also be substituted with the substituents specified herein, for example with 1, 2 or 3 substituents, in the same manner as substituted alkyl groups.

"Heterocyclic group", "heterocyclic", "heterocycle", "heterocyclyl", "heterocycloalkyl", or "heterocyclo" alone and when used as a moiety in a complex group are used interchangeably and refer to cycloalkyl group, i.e., any mono-, bi-, or tricyclic, saturated or unsaturated, non-aromatic ring systems having the number of atoms designated, generally from 5 to about 14 atoms, where the ring atoms are carbon and at least one heteroatom (nitrogen, sulfur or oxygen). In a particular embodiment the group incorporates 1 to 4 heteroatoms. Typically, a 5-membered ring has 0 to 2 double bonds and 6- or 7-membered ring has 0 to 3 double bonds and the nitrogen or sulfur heteroatoms may optionally be oxidized (e.g. SO, $SO_2$), and any nitrogen heteroatom may optionally be quaternized. Particular non-aromatic heterocycles include morpholinyl (morpholino), pyrrolidinyl, oxiranyl, oxetanyl, tetrahydrofuranyl, 2,3-dihydrofuranyl, 2H-pyranyl, tetrahydropyranyl, aziridinyl, azetidinyl, 1-methyl-2-pyrrolyl, piperazinyl and piperidinyl. For the avoidance of doubt, "heterocycloalkyl includes heterocycloalkyl alkyl.

"Heteroaryl" alone and when used as a moiety in a complex group refers to any aryl group, i.e., mono-, bi-, or tricyclic aromatic ring system having the number of atoms designated where at least one ring is a 5-, 6- or 7-membered ring containing from one to four heteroatoms selected from the group nitrogen, oxygen, and sulfur (Lang's Handbook of Chemistry, supra). Included in the definition are any bicyclic groups where any of the above heteroaryl rings are fused to a benzene ring. The following ring systems are examples of the heteroaryl (whether substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzofuryl, benzothiazolyl, benzothiadiazolyl, benzotriazolyl, benzoimidazolyl and indolyl. Particularly "heteroaryls" include; 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2 (n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5, 6-tetrahydro-4-(formylmethyl)-5,6-dioxo-as-triazin-3-yl, 2,5-dihydro-5-oxo-6-hydroxy-as-triazin-3-yl, 2,5-dihydro-5-oxo-6-hydroxy-as-triazin-3-yl sodium salt, 2,5-dihydro-5-oxo-6-hydroxy-2-methyl-as-triazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl. An alternative group of "heteroaryl" includes: 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,4-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

For the avoidance of doubt, aryl includes fused aryl which includes, for example, naphthyl, indenyl and also include arylalkyl; cycloalkyl includes fused cycloalkyl which includes, for example, tetrahydronaphthyl and indanyl; heteroaryl includes fused heteroaryl which includes, for example, indoyl, benzofuranyl, benzothienyl and also includes cycloalkylalkyl; heterocyclo includes fused heterocycloalkyl which includes, for example, indolinyl, isoindolinyl, tetrahydroquinolinyl, tetrahydroisoquinolinyl and also includes heterocycloalkylalkyl.

"Optionally substituted" means that a H atom can be, but is not necessarily, replaced by one or more different atoms. One of skill in the art will readily know, or can readily ascertain, what atoms or moieties can be substituted for a hydrogen atom or atoms in a given position. Typical optional substituents are any one or more of hydroxy, alkyl, lower alkyl, alkoxy, lower alkoxy, cycloalkyl, heterocycloalkyl, aryl, heteroaryl, halogen, pseudohalogen, haloalkyl, pseudohaloalkyl, carbonyl, carboxyl, mercapto, amino, nitro, and thiocarbonyl, but other moieties can also be optional substituents. So, for example, optionally substituted nitrogen can mean an amide, sulfonamide, urea, carbamate, alkylamines, dialkylamines, arylamines, etc; optionally substituted alkyl includes methyl, ethyl, propyl, isopropyl, t-butyl, etc.; optionally substituted aryl includes phenyl, benzyl, tolyl, pyridine, naphthyl, imidazole, etc. Reference to a group as "optionally substituted" encompasses that group when it is substituted as described above or, alternatively, when it is unsubstituted. When "optionally substituted" is used in front of or at the end of a listing of chemical groups, all such groups are optionally substituted (unless otherwise indicated by context.)

A "Linker" is a bond or linking group whereby two chemical moieties are directly covalently linked one to the other or are indirectly linked via a chemical moiety that covalently links the two chemical moieties, in either case, to form a homo- or heterodimer. A Linker (L) therefore, is a single, double, or triple covalent bond or is a contiguous chain, branched or unbranched, substituted or unsubstituted, of 1 to about 100 atoms, typically 1 to about 20 atoms and typically up to about 500 MW, e.g., alkyl, alkylene, alkylyne, alkyloxyalkyl, alkylarylalkyl, or optionally-substituted alkyl, alkylene, alkylyne, alkyloxyalkyl, alkylarylalkyl chain of 1 to 12 atoms. Illustrative Linkers are described, e.g., in US 20050197403 as well as in U.S. patent application Ser. No. 11/363,387 filed Feb. 27, 2006, both of which are incorporated herein by reference as though fully set forth.

"Pseudohalogens" are binary inorganic compounds of the general form XY, where X is a cyanide, cyanate, thiocyanate etc. group and Y is any of X, or a true halogen. Not all combinations are known to be stable. Examples include cyanogen, $(CN)_2$ and iodine cyanide, ICN. These anions behave as halogens and the presence of the internal double bonds or triple bonds do not appear to affect their chemical behavior.

"Inhibitor" or "antagonists" means a compound which reduces or prevents the binding of IAP proteins to caspase proteins or which reduces or prevents the inhibition of apoptosis by an IAP protein, or which binds to an IAP BIR domain in a manner similar to the amino terminal portion of Smac, thereby freeing Smac to inhibit the action of an IAP.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

DETAILED DESCRIPTION OF THE PREFERRED EMBODIMENTS

It must also be noted that as used herein and in the appended claims, the singular forms "a", "an", and "the" include plural reference unless the context clearly dictates otherwise. Unless defined otherwise, all technical and scientific terms used herein have the same meanings as commonly understood by one of ordinary skill in the art. Although any methods similar or equivalent to those described herein can be used in the practice or testing of embodiments of the present invention, the preferred methods are now described. All publications and references mentioned herein are incorporated by reference. Nothing herein is to be construed as an admission that the invention is not entitled to antedate such disclosure by virtue of prior invention.

The terms "mimetic," "peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics, as further described below.

As used herein, the terms "pharmaceutically acceptable", "physiologically tolerable" and grammatical variations thereof, as they refer to compositions, carriers, diluents and reagents, are used interchangeably and represent that the materials can be administered to a human being.

As used herein "subject" or "patient" refers to an animal or mammal including, but not limited to, human, dog, cat, horse, cow, pig, sheep, goat, chicken, monkey, rabbit, rat, mouse, etc.

As used herein, the term "therapeutic" means an agent utilized to treat, combat, ameliorate, prevent or improve an unwanted condition or disease of a patient. Embodiments of the present invention are directed to promote apoptosis, and thus cell death.

The terms "therapeutically effective amount" or "effective amount", as used herein, may be used interchangeably and refer to an amount of a therapeutic compound component of the present invention. For example, a therapeutically effective amount of a therapeutic compound is a predetermined amount calculated to achieve the desired effect, i.e., to effectively promote apoptosis, preferably by eliminating an IAP inhibition of apoptosis, more preferably by inhibiting an IAP binding to a caspase.

It has been demonstrated in accordance with the present invention that the IAP-binding compounds of the present invention are capable of potentiating apoptosis of cells.

Optionally substituted 5-, 6-, or 7-membered heterocycloalkyl groups with at least one N or O atom in the ring that are useful in the practice of the invention include, for example, pyrrolidine, piperidine, perhydroazapine rings, or monosaccharides or disaccharides, each unit comprising three to six carbon atoms, although longer chain polysaccharides can also be employed. These include, for example, trioses, tetroses, pentoses, and hexoses, such as glucose, mannose, fructose, xylose, erythrose, fucose, galactose, etc. The sugars can be naturally-occurring (including D- and L-sugars) or non-naturally-occurring sugars or derivatives thereof and can be the alpha or beta anomers. Heteroaryl groups with at least one N atom in the ring that are useful in the practice of the invention include, for example, pyridine, pyrimidine, or pyrazine.

Chemical procedures for synthesizing or derivatizing, or modifying, Smac mimetics by binding an optionally substituted 5-, 6-, or 7-membered heterocycloalkyl group with at least one N or O atom in the ring or a heteroaryl group with at least one N atom in the ring thereto are known to person of skill in the art or can be determined without undue experimentation.

Monomeric IAP antagonists of the invention include compounds of formula I:

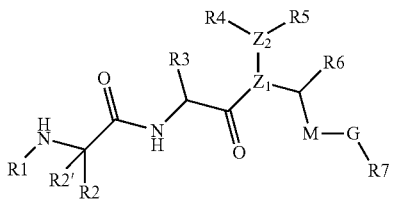

I wherein $Z_1$ and $Z_2$ are each independently CH or N;

$R_1$ is H or optionally substituted hydroxy, alkyl, cycloalkyl, heterocycloalkyl, aryl, or heteroaryl; and when $R_2'$ is H then $R_2$ and $R_1$ can together form an aziridine or azetidine ring;

$R_2$ and $R_2'$ are each independently H or optionally substituted alkyl, cycloalkyl, or heterocycloalkyl; or when $R_2'$ is H then $R_2$ and $R_1$ can together form an aziridine or azetidine ring;

$R_3$ and $R_4$ are each independently H or optionally substituted alkyl, cycloalkyl, heterocycloalkyl, aryl, or heteroaryl; or, $R_3$ and $R_4$ are each carbon and are linked by a covalent bond or by an optionally-substituted alkylene or alkenylene group of 1 to 8 carbon atoms where one to three carbon atoms can be replaced by N, O, $S(O)_n$, or C=O;

$R_5$ and $R_6$ are each independently H or optionally substituted hydroxy, alkyl, cycloalkyl, heterocycloalkyl, aryl, or heteroaryl; or $R_5$ and $R_6$ are each carbon and are linked by a covalent bond or by an optionally-substituted alkylene or alkenylene group of 1 to 8 carbon atoms where one to three carbon atoms can be replaced by N, O, $S(O)_n$, or C=O;

M is a bond or an optionally substituted alkylene group of 1 to 5 carbon atoms;

G is a bond, a heteroatom, —(C=O)—, —$S(O)_n$—, —$NR_8$—, —$NCOR_8$—, or —$NS(O)_nR_8$—, where $R_8$ is lower alkyl, optionally-substituted lower alkyl or $C_{3-8}$ cycloalkyl;

$R_7$ is optionally substituted alkyl, cycloalkyl, heterocycloalkyl, aryl, or heteroaryl, wherein $R_7$ is substituted with -$L_1$-$R_{10}$ and is optionally further substituted;

$L_1$ is a covalent bond or optionally substituted $C_1$-$C_6$ alkylene;

$R_{10}$ is an optionally substituted 5-, 6-, or 7-membered heterocycloalkyl group with at least one N or O atom in the ring or $R_{10}$ is a heteroaryl group with at least one N atom in the ring;

n can be the same or different in each usage and is 0, 1, or 2;

and pharmaceutically acceptable salts and solvates thereof.

In illustrative embodiments of compounds of Formula I, when $Z_1$ is N and $Z_2$ is CH, then at least one of the following is true:

(i) $R_5$ and $R_6$ together are not both carbon atoms linked by a single covalent bond;

(ii) $R_5$ and $R_6$ are both carbon atoms linked by a single covalent bond and $R_5$ is disubstituted;

(iii) $R_5$ and $R_6$ are both carbon atoms linked by a single covalent bond and $R_6$ is mono- or disubstituted;

(iv) $R_5$ and $R_6$ are both carbon atoms linked by a single covalent bond and $R_3$ and $R_4$ are both carbon atoms linked by a covalent bond or by an optionally-substituted alkylene or alkenylene group of 1 to 8 carbon atoms where one to three carbon atoms can be replaced by N, O, $S(O)_n$, or C=O.

In illustrative embodiments of compounds of Formula I, one or any two or more of the following limitations apply to compounds in which the preceding limitations on $R_5$ and $R_6$ apply or in which the preceding limitations on $R_5$ and $R_6$ don't apply:

(1) M is optionally-substituted $C_1$-$C_5$ alkylene, alkenylene, or alkynylene; or M is $C_1$-$C_3$ alkylene optionally-substituted with lower alkyl; or M is $C_1$-$C_3$ alkylene (excluding alkenylene and alkynylene) optionally-substituted with lower alkyl;

(2) G is a bond;

(3) $R_7$ is aryl or heteroaryl;

(4) $L_1$ is a covalent bond or $C_1$-$C_4$ alkylene; or $L_1$ is a single covalent bond;

(5) $R_{10}$ is a tetrahydrofuranyl or tetrahydropyranyl moiety optionally substituted with hydroxy, lower alkyl, lower alkoxy, or optionally-substituted lower alkoxy selected from arylalkyloxy, alkylcarbonyloxy, arylcarbonyloxy, acetyloxy; or, $R_{10}$ is an optionally-substituted nitrogen-containing 5- to 7-membered heteroaryl or heterocycloalkyl group; or $R_{10}$ is tetrahydrofuranyl or tetrahydropyranyl substituted with at least one hydroxy or acetyloxy group; or $R_{10}$ is a 5- to 7-membered heteroaryl or heterocycloalkyl group having a single nitrogen atom in the ring and no additional heteroatoms (6) $R_1$ is H, methyl, allyl, propargyl, ethyl, cycloalkyl, hydroxyethyl or cycloalkylmethyl; or $R_1$ is H, methyl, allyl, propargyl, ethyl, cycloalkyl, hydroxy ethyl or cycloalkylmethyl;

(7) $R_2$ and $R_2'$ are independently H, methyl, fluoromethyl, difluoromethyl, ethyl, hydroxyethyl, fluoroethyl, and cycloalkyl; or $R_2$ and $R_2'$ are independently H, methyl, fluoromethyl, difluoromethyl, ethyl, hydroxyethyl, fluoroethyl, and cycloalkyl;

(8) $R_3$ and $R_4$ are independently H, methyl, ethyl, isopropyl, isobutyl, sec-butyl, tert-butyl, cycloalkyl, heterocycloalkyl, aryl, or heteroaryl, optionally-substituted with hydroxyl, mercapto, sulfonyl, alkylsulfonyl, halogen, pseudohalogen, amino, carboxyl, alkyl, haloalkyl, pseudohaloalkyl, alkoxy, or alkylthio, or $R_3$ and $R_4$ are carbon atoms and are linked by a covalent bond or by an optionally-substituted alkylene or alkenylene group of 1 to 3 carbon atoms of which 1 or more atoms can be replaced by N, O, $S(O)_n$, or C=O; or $R_3$ and $R_4$ are linked by a covalent bond or by an optionally-substituted alkylene or alkenylene group of 1 to 3 carbon atoms of which 1 or more atoms can be replaced by N, O, $S(O)_n$, or C=O;

(9) $R_5$ and $R_6$ are independently optionally substituted lower alkyl or $C_3$-$C_8$ cycloalkyl wherein the optional substituents are hydroxy or lower alkoxy, or $R_5$ and $R_6$ are carbon atoms and are linked by a covalent bond or by an optionally-substituted alkylene or alkenylene group of 1 to 3 carbon atoms of which 1 or more atoms can be replaced by N, O, $S(O)_n$, or C=O;

(10) $R_7$ is IIa or IIb:

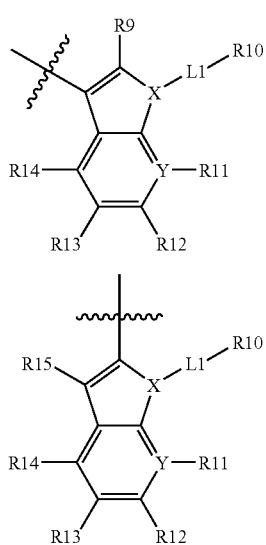

wherein L1 is a single covalent bond
X is —N—, —C=C($R_{16}$)—, —N=C— or —C(O)N—;
Y is —C—, —N—, or —N⁺—; such that,
When Y is —C— then $R_9$, $R_{11}$, $R_{12}$, $R_{13}$, $R_{14}$, $R_{15}$, and $R_{16}$ are, independently, —H, halogen, or optionally substituted alkyl, cycloalkyl, heterocycloalkyl, aryl, heteroaryl, hydroxy, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime; provided that when X is —N— or —C(O)—N—, -L1-$R_{10}$ is bound to the —N— atom; and, when X is —C=C($R_{16}$)— or —N=C—, -L1-$R_{10}$ is bound to the —C= atom; and When Y is —N— or —N⁺—, then R11 is absent or —O⁻, and $R_9$, $R_{12}$, $R_{13}$, $R_{14}$, $R_{15}$, and $R_{16}$ are, independently, —H, halogen, or optionally substituted alkyl, cycloalkyl, heterocycloalkyl, aryl, heteroaryl, hydroxyl, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime; provided that when X is —N— or —C(O)—N—, -L1-$R_{10}$ is bound to the —N— atom; and, when X is —C=C($R_{16}$)— or —N=C—, -L1-$R_{10}$ is bound to the —C= atom; or

(11) $R_7$ is IIa or IIb;
X is —N—;
Y is —C—, —N—, or —N⁺—; such that
When Y is —C—, then $R_9$, $R_{11}$, $R_{12}$, $R_{13}$, $R_{14}$ and $R_{15}$ are, independently, —H, halogen, or optionally substituted alkyl, cycloalkyl, heterocycloalkyl, aryl, heteroaryl, hydroxyl, alkoxy, polyalkylether, amino, alkylamino, dialkylamino, alkoxyalkyl, sulfonate, aryloxy or heteroaryloxy;

When Y is —N—, then $R_{11}$ is absent, and $R_9$, $R_{12}$, $R_{13}$, $R_{14}$ and $R_{15}$ are, independently, —H, halogen, or optionally substituted alkyl, cycloalkyl, heterocycloalkyl, aryl, heteroaryl, hydroxyl, alkoxy, polyalkylether, amino, alkylamino, dialkylamino, alkoxyalkyl, sulfonate, aryloxy or heteroaryloxy;

When Y is —N⁺—, then $R_{11}$ is —O⁻, and $R_9$, $R_{12}$, $R_{13}$, $R_{14}$ and $R_{15}$ are, independently, —H, halogen, or optionally substituted alkyl, cycloalkyl, heterocycloalkyl, aryl, heteroaryl, hydroxyl, alkoxy, polyalkylether, amino, alkylamino, dialkylamino, alkoxyalkyl, sulfonate, aryloxy or heteroaryloxy;

In illustrative embodiments, the compound of formula 1 as the formula (III):

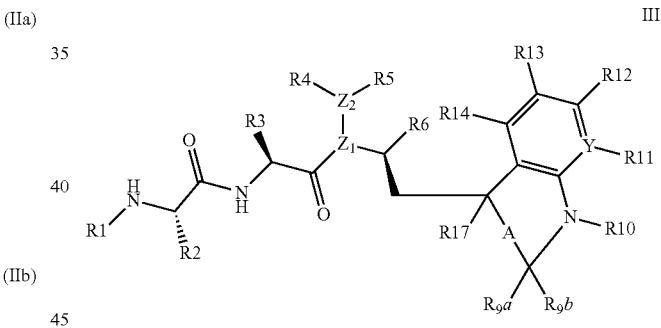

wherein Y is —C—, —N—, or —N⁺—; such that,
A is a single or double bond;
When A is a single bond and Y is —C— then $R_9a$, $R_9b$, $R_{11}$, $R_{12}$, $R_{13}$, $R_{14}$, and $R_{17}$ are, independently, —H, halogen, or optionally substituted alkyl, cycloalkyl, heterocycloalkyl, aryl, heteroaryl, hydroxy, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime;

When A is a single bond and Y is —N— or —N⁺—, then $R_{11}$ is absent or —O⁻, and $R_9a$, $R_9b$, $R_{12}$, $R_{13}$, $R_{14}$, and $R_{17}$ are, independently, —H, halogen, or optionally substituted alkyl, cycloalkyl, heterocycloalkyl, aryl, heteroaryl, hydroxy, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime;

When A is a double bond and Y is —C— then $R_9b$ and $R_{17}$ are absent; and $R_9a$, $R_{11}$, $R_{12}$, $R_{13}$, and $R_{14}$ are, independently, —H, halogen, or optionally substituted alkyl, cycloalkyl, heterocycloalkyl, aryl, heteroaryl, hydroxy, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime;

When A is a double bond and Y is —N— or —N+—, then $R_9b$ and $R_{17}$ are absent; and $R_{11}$ is absent or —O−, and $R_9a$, $R_{12}$, $R_{13}$, and $R_{14}$ are, independently, —H, halogen, or optionally substituted alkyl, cycloalkyl, heterocycloalkyl, aryl, heteroaryl, hydroxyl, alkoxy, polyalkylether, amino, alkylamino, dialkylamino, alkoxyalkyl, sulfonate, aryloxy, heteroaryloxy, acyl, acetyl, or carboxylate, sulfonate, sulfone, imine, or oxime;

Specific illustrative compounds of formula I include those shown below as compounds A through U and HH through SS.

Dimeric compounds of the invention include compounds of formula IV:

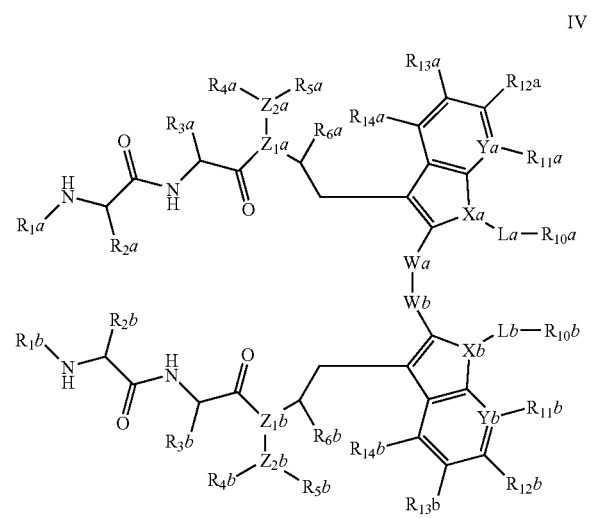

IV wherein $Z_1a$, $Z_2a$, $Z_1b$, and $Z_2b$ are independently CH or N;

$R_1a$ and $R_1b$ are independently H or optionally substituted hydroxyl, alkyl, cycloalkyl, heterocycloalkyl, aryl, or heteroaryl; and when $R_2a'$ is H then $R_2a$ and $R_1a$ can together form an aziridine or azetidine ring and when $R_2b'$ is H then $R_2b$ and $R_1b$ can together form an aziridine or azetidine ring;

$R_2a$, $R_2a'$, $R_2b$ and $R_2b'$ are independently H or optionally substituted alkyl, cycloalkyl, or heterocycloalkyl; or when $R_2a'$ is H then $R_2a$ and $R_1a$ can together form an aziridine or azetidine ring and when $R_2b'$ is H then $R_2b$ and $R_1b$ can together form an aziridine or azetidine ring;

$R_3a$, $R_3b$, $R_4a$ and $R_4b$ are independently H or optionally substituted alkyl, cycloalkyl, heterocycloalkyl, aryl, or heteroaryl; or, $R_4a$ and $R_3a$, or $R_4b$ and $R_3b$, or both, are carbon atoms linked by an optionally-substituted alkylene or alkenylene group of 1 to 8 carbon atoms where one to three carbon atoms can be replaced by N, O, S(O)$_n$, or C=O;

$R_5a$, $R_6a$, $R_5b$, and $R_6b$ are independently H or optionally substituted hydroxyl, alkyl, cycloalkyl, heterocycloalkyl, aryl, or heteroaryl; or $R_5a$ and $R_6a$ or $R_5b$ and $R_6b$, or both, are carbon atoms linked by an optionally-substituted alkylene or alkenylene group of 1 to 8 carbon atoms where one to three carbon atoms can be replaced by N, O, S(O)$_n$, C=O;

n can be the same or different in each usage and is 0, 1, or 2;

Xa is —O—, —N(La—$R_{10}$a)-, —S—, optionally-substituted —C(La—$R_{10}$a)=CH—, —C(O)—O—, —C(O)—N(La—$R_{10}$a)-, —N=C(La—$R_{10}$a)-;

Xb is —O—, —N(Lb-$R_{10}$b)-, —S—, optionally-substituted —C(Lb-$R_{10}$b)=CH—, —C(O)—O—, —C(O)—N(Lb-$R_{10}$b)-, —N=C(Lb-$R_{10}$b)-, provided that if Xb is —O—, —S—, or —C(O)—O—, then Xa is —N(La—$R_{10}$a)-, optionally-substituted —C(La—$R_{10}$a)=CH—, —C(O)—N(La—$R_{10}$a)-, or —N=C(La—$R_{10}$a)-, and if Xa is —O—, —S—, or —C(O)—O—, then Xb is —N(Lb-$R_{10}$b)-, optionally-substituted —C(Lb-$R_{10}$b)=CH—, —C(O)—N(Lb-$R_{10}$b)—, or —N=C(Lb-$R_{10}$b)-;

La and Lb are independently a covalent bond or $C_1$-$C_4$ alkylene;

$R_{10}a$ and $R_{10}b$ are independently an optionally substituted 5-, 6-, or 7-membered heterocycloalkyl with at least one N or O atom in the ring or heteroaryl with at least one N atom in the ring, provided that one but not both of $R_{10}a$ and $R_{10}b$ can optionally be —H;

Wa and Wb are together a Linker.

In illustrative embodiments, Xa is —N(La—$R_{10}$a)-, —C(La—$R_{10}$a)-, or —N=C(La—$R_{10}$a)-, Xb is —N—, La is a bond, —$R_{10}$a is an optionally substituted 5-, 6-, or 7-membered heterocycloalkyl with at least one N or O atom in the ring or heteroaryl with at least one N atom in the ring, and Lb is a bond, and —$R_{10}$b is H.

Any one or any two or more of the above limitations can also apply to compounds having formula IV. Other limitations that can apply to dimeric IAP antagonists of the invention include:

Wa and Wb together are a covalent bond or optionally substituted alkylene, cycloalkyl, or aryl, of 2 to 20 carbon atoms where one or more carbon atoms can be replaced with N, O, or S(O)$_n$; and Xa and Xb are independently —O—, —S—, or —C(O)—O—; or Wa and Wb together form a single covalent bond; and/or one of $R_{10}a$ and $R_{10}b$ is —H or, if Xa or Xb is —O—, —S—, or —C(O)—O—, then $R_{10}a$ or $R_{10}b$, respectively, is absent.

Illustrative embodiments have the following formulae:

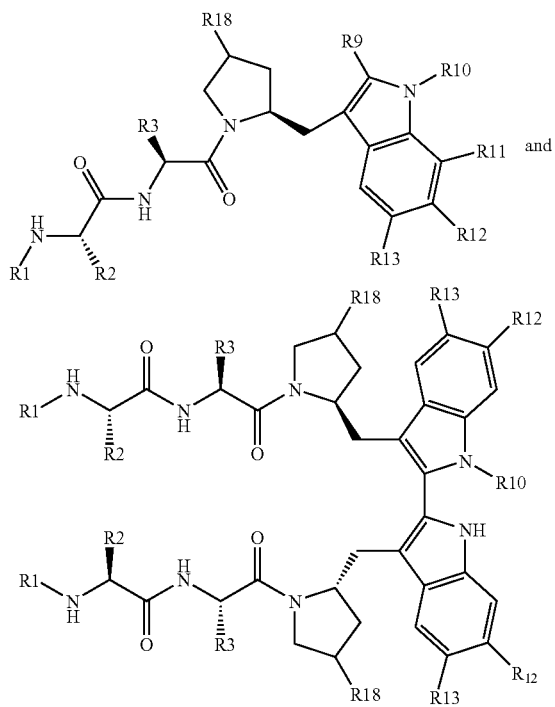

wherein $R_1$, $R_2$, and $R_3$ are independently lower alkyl, lower alkoxy, lower alkanol, or $C_3$-$C_6$ cycloalkyl; $R_{18}$ is H or OH; $R_{11}$, $R_{12}$, and $R_{13}$ are independently H or halogen and $R_{10}$ is an optionally substituted 5-, 6-, or 7-membered heterocycloalkyl with at least one N or O atom in the ring or $R_{10}$ is heteroaryl with at least one N atom in the ring.

Specific illustrative compounds of formula IV include those shown below as compounds V through GG.

Following are illustrative schemes illustrating preparation of modified monomers and dimers. Using similar synthetic techniques, the sugar-modified Smac mimetics shown in Tables 1 and 2, below, and the piperidine-substituted Smac mimetics shown in Table 3, below, were prepared.

The binding affinity of illustrative compounds of the present invention to an IAP was determined substantially as described by Nikolovska-Coleska, Z. et. al. (Analytical Biochemistry (2004), vol. 332:261-273) using a variety of fluorogenic substrates and is reported as a Kd value. Briefly, various concentrations of IAP antagonists were mixed with 5 nM fluorescently labeled peptide (AbuRPF-K(5-Fam)-NH$_2$) and 40 nM of an IAP-BIR3 for 15 min at RT in 100 mL of 0.1M Potassium Phosphate buffer, pH 7.5 containing 100 mg/ml bovine g-globulin. Following incubation, the polarization values (mP) were measured on a Victor2V using a 485 nm excitation filter and a 520 nm emission filter. IC50 values were determined from the plot using nonlinear least-squares analysis using GraphPad Prism. The compounds described herein afford Kd values in the ranges of: Kd<0.1 μM (A), Kd=0.1-1 μM (B), Kd=1-10 μM (C), and Kd>10 μM (D).

Abbreviations used in the following preparations, which are illustrative of synthesis of compounds of the invention generally, are: Cbz: Benzyloxycarbonyl; Boc: tert-butyloxycarbonyl; THF: tetrahydrofuran; DCM: dichloromethane; DDQ: 2,3-dichloro-5,6-dicyano-1,4-benzoquinone; NMP: N-methylpyrrolidinone; DMF: dimethylformamide; TFA: trifluoroacetic acid; HOAc or AcOH: acetic acid; Hex: hexanes; HPLC: high performance liquid chromatography; TLC: thin layer chromatography; EtOAc: ethyl acetate; DIPEA: diisopropylethylamine; TEA: triethylamine; HATU: 2-(7-Aza-1H-benzotriazole-1-yl)-1,1,3,3-tetramethyluronium hexafluorophosphate.

Preparation of Monomeric IAP Antagonists. (Formula 13, Below. Referred to as Compound A in Table 1, Below.)

Scheme I

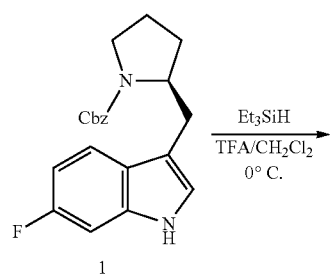

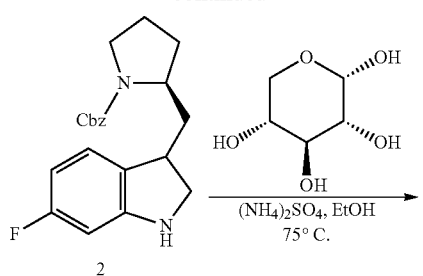

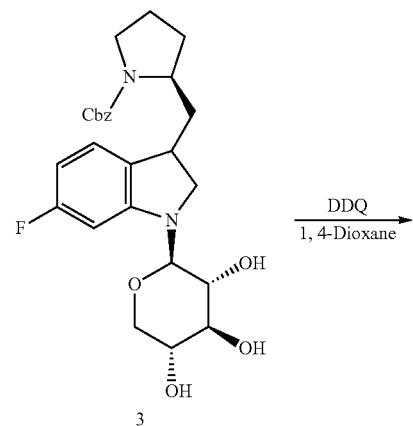

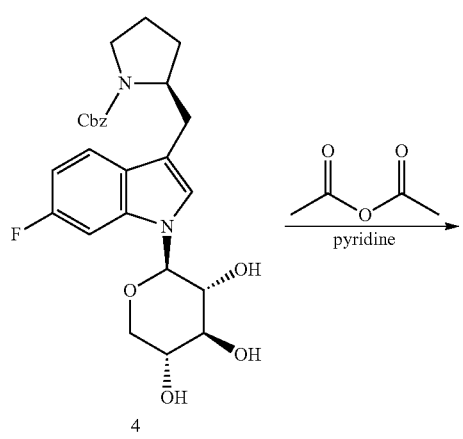

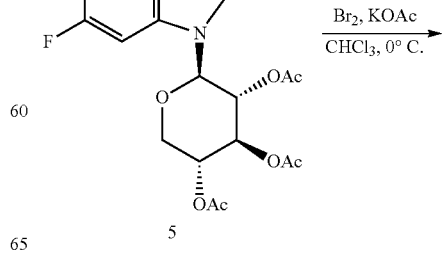

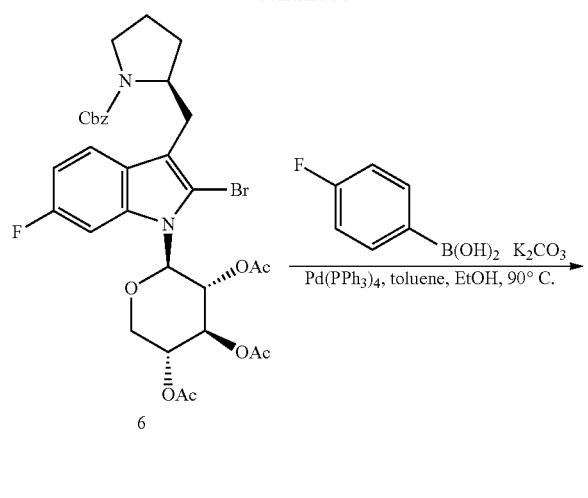
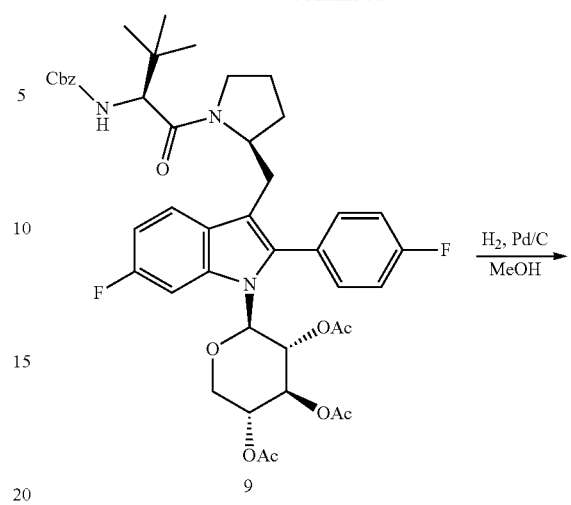
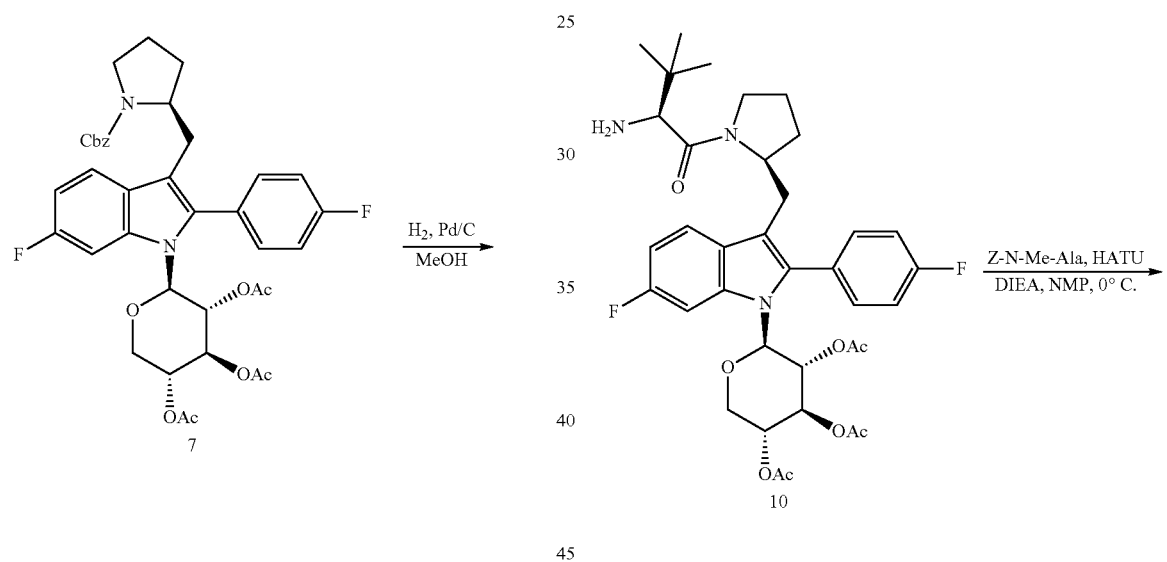
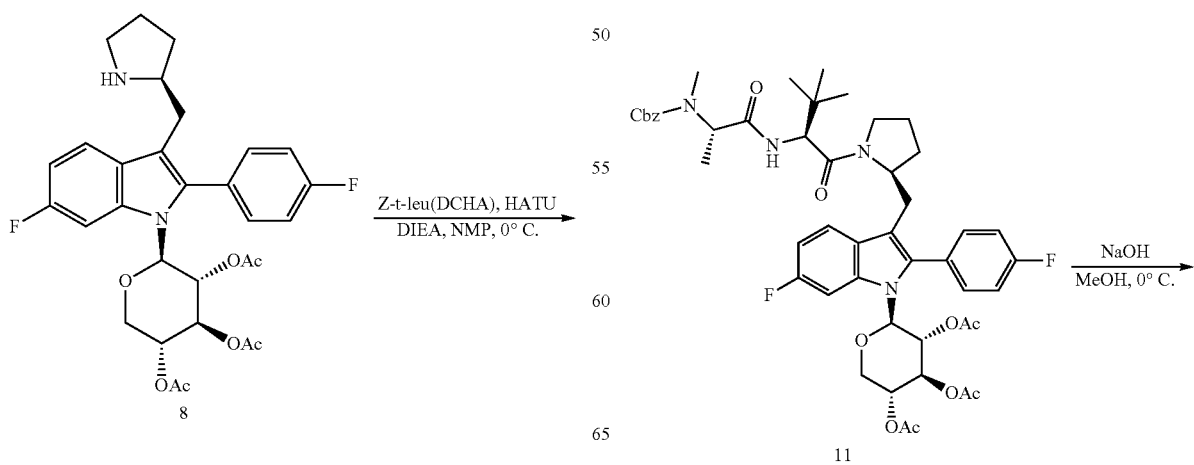

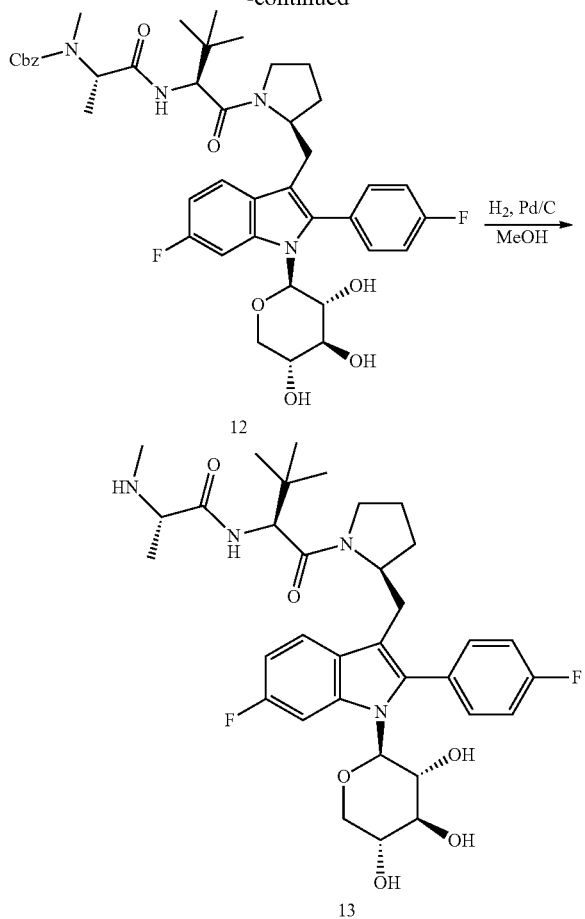

3.87 (m, 3H), 3.79-3.56 (m, 4H), 3.48-3.29 (m, 6H), 2.29-1.92 (m, 4H), 1.77-1.28 (m, 2H) ppm.

Substituted Indole (4):

To a solution of 3 (0.98 g, 2.01 mmol) in anhydrous 1,4-dioxane (30 mL) was added 2,3-dichloro-5,6-dicyano-1,4-benzoquinone (0.55 g, 2.42 mmol) neat in one portion. The reaction was stirred at room temperature for 30 min. Thin layer chromatography (10% MeOH/CH$_2$Cl$_2$) indicated no remaining 3. The reaction mixture was filtered and the solid washed with EtOAc. The filtrate was washed with saturated NaHCO$_3$ (4×), brine, dried over Na$_2$SO$_4$, filtered, and concentrated. Purification by column chromatography on silica gel (2% MeOH/CH$_2$Cl$_2$ to 5% MeOH/CH$_2$Cl$_2$) afforded 4 as a white solid (0.792 g, 81%). $^1$H NMR (CDCl$_3$, 300 MHz) δ7.49-7.44 (m, 1H), 7.34-7.29 (m, 5H), 7.18-7.02 (m, 1H), 6.86 (t, J=3.0 Hz, 1H), 6.73-6.67 (m, 1H), 5.10-5.01 (m, 2H), 4.90-4.88 (m, 2H), 4.33-4.18 (m, 2H), 4.06-3.59 (m, 6H), 3.41-3.06 (m, 3H), 2.92-2.55 (m, 3H), 1.94-1.25 (m, 2H) ppm.

Peracetylated Intermediate (5):

To a solution of 4 (0.79 g, 1.63 mmol) in pyridine (8 mL) was added acetic anhydride (1.66 g, 1.54 mL, 16.3 mmol) and the reaction was stirred at room temperature for 6 hours. Thin layer chromatography (1/1 Hex/EA) indicated no remaining 4. The reaction was diluted with ethyl acetate and washed with 1M HCl (3×), water, saturated NaHCO$_3$, brine, dried over Na$_2$SO$_{41}$ filtered, and concentrated. Purification by column chromatography on silica gel (1/1 Hex/EtOAc) afforded 5 as a foamy solid (0.86 g, 86%). $^1$H NMR (CDCl$_3$, MHz) δ7.72 (t, J=2.5 Hz, 1H), 7.45-7.36 (m, 5H), 7.11-6.86 (m, 2H), 6.61 (t, J=3.0 Hz, 1H), 5.42-5.36 (m, 3H), 5.25-5.17 (m, 3H), 4.29-4.23 (m, 1H), 4.16-4.09 (m, 1H), 3.59-3.10 (m, 4H), 2.66-2.49 (m, 1H), 2.08 (s, 3H), 2.05 (s, 3H), 1.88-1.61 (m, 6H) ppm.

Bromo Derivative (6):

A mixture of 5 (0.20 g, 0.327 mmol) and potassium acetate (0.096 g, 0.981 mmol) in chloroform (10 mL) was cooled to 0 C and a solution of bromine (0.063 g, 0.02 mL, 0.393 mmol) in chloroform (1 mL) was added dropwise via syringe. The reaction was stirred at 0 C for 20 min. Thin layer chromatography (1/1 Hex/EA) indicated no remaining 5. The reaction was diluted with brine and dichloromethane. The layers were separated and the organics were washed with saturated Na$_2$S$_2$O$_3$, brine, dried over Na$_2$SO$_4$, filtered, and concentrated. Purification by column chromatography on silica gel (1/1 Hex/EtOAc) afforded 6 as a foamy solid (0.206 g, 91%). $^1$H NMR (CDCl$_3$, 300 MHz) δ7.69 (m, 1H), 7.46-7.35 (m, 5H), 6.91 (t, J=3.0 Hz, 1H), 6.61 (t, J=3.0 Hz, 1H), 5.58-5.39 (m, 3H), 5.26-5.08 (m, 3H), 4.37-4.32 (m, 1H), 4.19-4.09 (m, 1H), 3.61-3.07 (m, 4H), 2.71-2.55 (m, 1H), 2.09 (s, 3H), 2.05 (s, 3H), 1.96-1.51 (m, 6H) ppm.

2-Arylindole Intermediate (7):

A mixture of 6 (0.21 g, 0.297 mmol), potassium carbonate (0.14 g, 1.04 mmol), and 4-fluorobenzeneboronic acid (0.054 g, 0.386 mmol) in toluene (12 mL) and ethanol (6 mL) was degassed by pulling a vacuum until bubbling occurred. Added next was tetrakis-triphenylphosphine palladium (0) (0.017 g, 0.015 mmol) and the mixture was degassed again, placed in an oil bath preheated at 90 C, and stirred for 3 hours. Thin layer chromatography (2/1 Hex/EA) indicated no remaining 6. The reaction was cooled to room temperature, diluted with ethyl acetate and washed with 1 M HCl, brine, dried over Na$_2$SO$_4$, filtered, and concentrated. Purification by column chromatography on silica gel (2/1 Hex/EtOAc) afforded 7 as a yellow solid (0.048 g, 23%). $^1$H NMR (CDCl$_3$, 300 MHz) δ7.88-7.75 (m, 1H), 7.40-7.19 (m, 9H), 7.01-6.91 (m, 1H), 6.65 (t, J=3.1 Hz, 1H), 5.61-5.41 (m, 3H), 5.29-4.93 (m, 3H), Indoline (2): A round bottom flask containing trifluoroacetic acid (60 mL) was cooled to 0 C under nitrogen and triethylsilane (1.16 g, 1.6 mL, 9.96 mmol) was added followed by the dropwise addition of indole 1 (1.17 g, 3.32 mmol; prepared using a modification of the procedure reported by Macor, et al. J. Med. Chem. 1992, 35, 4503-4505) in 9 mL dry dichloromethane, added over 1 hour. Following complete addition, the solution was stirred for 10 min. Thin layer chromatography (2/1 Hex/EA) indicated no remaining 1. The solvent was removed in vacuo and the residue was dissolved in EtOAc. The organic layer was washed with saturated NaHCO$_3$ (2×), and brine. The EtOAc layer was dried over Na$_2$SO$_4$, filtered, and concentrated. Purification by column chromatography on silica gel (2/1 hexane/ethyl acetate) afforded 2 as a yellow oil (0.79 g, 67%). $^1$H NMR (CDCl$_3$, 300 MHz) δ7.34-7.31 (m, 5H) 6.99-6.85 (m, 1H)/6.34-6.27 (m, 2H), 5.12 (s, 2H), 4.13-3.71 (m, 2H), 3.58-3.16 (m, 5H), 2.05-1.87 (m, 4H), 1.73-1.57 (m, 2H) ppm.

N-Substituted Indoline (3):

A mixture of compound 2 (0.79 g, 2.23 mmol), D-(+)-Xylose (1.0 g, 6.69 mmol), and ammonium sulfate (0.88 g, 6.69 mmol) in ethanol (50 mL) was heated at 75 C overnight. Thin layer chromatography (10% MeOH/CH$_2$Cl$_2$) indicated no remaining 2. The reaction mixture was preabsorbed on to silica gel and purified by column chromatography on silica gel (2% MeOH/CH$_2$Cl$_2$ to 59 MeOH/CH$_2$Cl$_2$) to afford compound 3 as a yellow solid (0.98 g, 90%). $^1$H NMR (CDCl$_3$, 300 MHz) δ7.33-7.31 (m, 5H), 6.91 (t, J=2.4 Hz, 1H), 6.39-6.27 (m, 2H), 5.12-4.99 (m, 3H), 4.62-4.45 (m, 1H), 4.05-

4.37-4.32 (m, 1H), 4.13-4.05 (m, 1H), 3.56-3.35 (m, 4H), 2.77-2.49 (m, 1H), 2.09 (s, 3H), 2.04 (s, 3H), 1.76-1.39 (m, 6H) ppm.

Unprotected Pyrrolidine (8):

A mixture of 7 (0.090 g, 0.128 mmol) and 10% palladium on activated carbon (0.020 mg, 20 wt %) in methanol (8 mL) was shaken under a hydrogen atmosphere at 45 psi on a Parr hydrogenator for 2 hours. Thin layer chromatography (10% MeOH/CH$_2$Cl$_2$) indicated no remaining 7. The mixture was filtered through a 0.45 uM filtering disk and washed with MeOH. The filtrate was concentrated and dried under high vacuum to give 8 as a white solid (0.049 g, 67%). $^1$H NMR (CDCl$_3$, 300 MHz) δ7.55-7.47 (m, 1H), 7.32-7.27 (m, 2H), 7.23-7.17 (m, 3H), 6.94 (t, J=3.0 Hz, 1H), 5.66 (m, 1H), 5.17-5.11 (m, 2H), 4.27 (m, 1H), 3.39-3.22 (m, 2H), 3.01-2.87 (m, 1H), 2.76-2.65 (m, 1H), 2.05 (s, 3H), 1.99 (s, 3H), 1.72-1.47 (m, 6H) ppm.

N-Acylated Intermediate (9):

A solution of CBZ-L-tert-leucine dicyclohexylamine salt (0.057 g, 0.129 mmol) and HATU (0.049 g, 0.129 mmol) in dry 1-methyl-2-pyrrolidinone (NMP) (2 mL) was cooled to 0 C and diisopropylethyl amine (0.022 g, 0.03 mL, 0.172 mmol) was added. After stirring for 15 min a solution of 8 (0.049 g, 0.086 mmol) in NMP (2 mL) was added and the reaction was stirred at 0 C for 2 hours followed by room temperature for 1 hour. Thin layer chromatography (2/1 Hex/EA) indicated no remaining 8. The reaction was diluted with ether and washed with 1 M HCl, water, saturated NaHCO$_3$, brine, dried over Na$_2$SO$_4$, filtered, and concentrated. Purification by column chromatography on silica gel (2/1 Hex/EtOAc) afforded 9 as a foamy solid (0.041 g, 58%). $^1$H NMR (CDCl$_3$, 300 MHz) δ8.74 (d, J=1.3 Hz, 1H), 8.43 (dd, J=0.04, 1.8 Hz, 1H), 8.03-7.98 (m, 1H), 7.47-7.43 (m, 1H), 7.39-7.35 (m, 8H), 7.02-6.97 (m, 1H), 5.62-5.59 (m, 1H), 5.42-5.36 (m, 1H), 5.20-5.06 (m 4H), 4.33-4.29 (m, 1H), 3.61-3.29 (m, 2H), 2.09-1.98 (m, 3H) 1.75-1.69 (m, 2H), 1.56 (m, 6H), 1.25-1.21 (m, 6H), 1.04-0.97 (m, 6H) ppm.

Free Amine (10):

A mixture of 9 (0.041 g, 0.050 mmol) and 10% palladium on activated carbon (0.010 mg, 20 wt 9) in methanol (8 mL) was shaken under a hydrogen atmosphere at 45 psi on a Parr hydrogenation apparatus for 2 hours. Thin layer chromatography (10% MeOH/CH$_2$Cl$_2$) indicated no remaining 9. The mixture was filtered through a 0.45 M filtering disk and washed with MeOH. The filtrate was concentrated and dried under high vacuum to give 10 as a white solid (0.034 g, 99%). Mass spectrum, m/z=684 [M+H]+.

Cbz-Protected Dipeptide (11):

A solution of Cbz-N-methyl-L-alanine (0.018 g, 0.074 mmol) and HATU (0.028 g, 0.074 mmol) in dry 1-methyl-2-pyrrolidinone (NMP) (1 mL) was cooled to 0 C and diisopropylethyl amine (0.012 g, 0.02 mL, 0.099 mmol) was added. After stirring for 15 min, a solution of 10 (0.034 g, 0.0497 mmol) in NMP (2 mL) was added and the reaction was stirred at 0 C for 2 hours followed by room temperature for 1 hour. Thin layer chromatography (1/1 Hex/EA) indicated no remaining 10. The reaction was diluted with ether and washed with 1 M HCl, water, saturated NaHCO$_3$, brine, dried over Na$_2$SO$_4$, filtered, and concentrated to afford 11 as a foamy solid (0.044 g, 98% crude). $^1$H NMR (CDCl$_3$, 300 MHz) δ8.06-7.97 (m, 1H), 7.39-7.33 (m, 9H), 7.27-7.22 (m, 1H), 7.01-6.96 (m, 1H), 5.65 (m, 1H), 5.20-5.10 (m 4H), 5.05-5.00 (m, 2H), 3.94-3.89 (m, 1H), 3.65-3.59 (m, 1H), 2.88-2.80 (m, 6H), 2.08-1.98 (m, 6H), 1.37-1.23 (m, 6H), 1.04-0.97 (m, 6H), 1.05-0.90 (m, 1H) ppm.

Hydroxylated Intermediate (12):

A solution of 11 (0.044 g, 0.049 mmol) in methanol (2 mL) was cooled to 0 C and 1M sodium hydroxide (0.16 mL, 0.16 mmol) was added. The reaction was stirred for 45 minutes. Thin layer chromatography (10% MeOH/CH$_2$Cl$_2$) indicated no remaining 11. The reaction was diluted with brine and saturated ammonium chloride solution and extracted with ethyl acetate (3×). The organic phase was dried over Na$_2$SO$_4$, filtered, and concentrated. The crude product 12 (0.037 g) was taken on without further purification. Mass spectrum, m/z=777.8 [M+H]+.

Final Dipeptide (13):

A mixture of 12 (0.037 g, 0.049 mmol) and lot palladium on activated carbon (0.010 mg, 20 wt t) in methanol (8 mL) was shaken under a hydrogen atmosphere at 45 psi on a Parr hydrogenation apparatus for 1.5 h. Thin layer chromatography (10% MeOH/CH$_2$Cl$_2$) indicated no remaining 12. The mixture was filtered through a 0.45 M filtering disk and washed with MeOH. Purification by reverse phase HPLC and lypholization gave 13 as the monoacetate salt (0.0107 g, 34%). $^1$H NMR (CDCl$_3$, 300 MHz) δ7.99-7.95 (m, 1H), 7.43-7.31 (m, 3H), 7.24-7.18 (m, 1H), 7.01-6.94 (m, 1H), 4.85-4.82 (m, 1H), 4.45 (m 1H), 4.12 (m, 2H), 3.39-3.37 (m, 3H), 3.32-3.20 (m, 4H), 2.41-2.28 (m, 4H), 2.03 (br s, 4H), 1.70 (m, 1H), 1.51 (m, 2H), 1.37-1.27 (m, 3H), 1.05-0.98 (m, 9H) ppm. Mass spectrum, m/z=643.6 [M+H]+.

TABLE 1

Binding of Monomeric IAP Antagonists to XIAP BIR3.

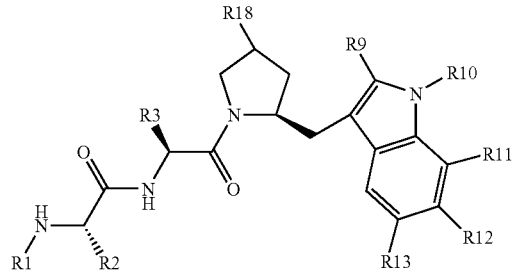

| Compound | R1 | R2 | R3 | R18 | R9 | R13 | R12 | R11 | R10 | K$_D$, µM |
|---|---|---|---|---|---|---|---|---|---|---|
| A | Me | Me | tBu | H | 4-F-phenyl | H | F | H | D-xylose | A |
| B | Me | Me | iPr | H | 4-F-phenyl | H | F | H | D-xylose | A |
| C | Me | Me | tBu | H | 4-F-phenyl | H | F | H | L-fucose | A |
| D | Me | Me | iPr | H | H | H | H | Me | L-fucose | B |
| E | Me | Me | iPr | H | H | H | H | Me | D-xylose | B |
| F | Me | Me | tBu | H | H | H | F | H | L-fucose | A |

TABLE 1-continued

Binding of Monomeric IAP Antagonists to XIAP BIR3.

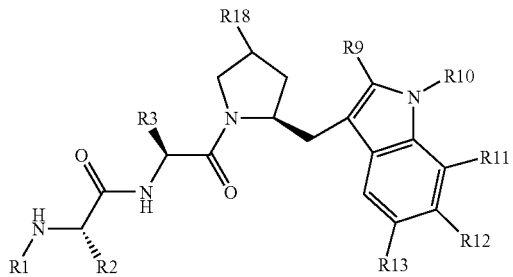

| Compound | R1 | R2 | R3 | R18 | R9 | R13 | R12 | R11 | R10 | $K_D$, μM |
|---|---|---|---|---|---|---|---|---|---|---|
| G | Me | Me | cHex | H | H | H | F | H | L-fucose | A |
| H | Me | Me | iPr | H | H | H | F | H | L-fucose | A |
| I | Me | Me | iPr | H | H | H | F | H | D-xylose | A |
| J | Me | Me | iPr | H | H | H | F | H | D-glucose | A |
| K | Me | Me | iPr | H | H | H | F | H | D-galactose | A |
| L | Me | Me | iPr | H | H | H | F | H | D-galactose tetra acetate | A |
| M | Me | Me | cHex | H | H | H | F | H | D-xylose | B |
| N | Me | Me | tBu | H | H | H | F | H | D-xylose | A |
| O | Me | Me | R-(Me)CHOMe | H | 4-F-phenyl | H | F | H | L-fucose | A |
| P | Me | Me | R-(Me)CHOMe | S-OH | 4-F-phenyl | Me | H | H | L-fucose | B |
| Q | Me | Me | tert-Butyl | S-OH | 4-F-phenyl | Me | H | H | L-fucose | B |
| R | Me | Me | R-(Me)CHOMe | H | 4-F-phenyl | Me | H | H | L-fucose | B |
| S | Me | Me | tert-Butyl | H | 4-F-phenyl | Me | H | H | L-fucose | B |
| T | Me | Me | tert-Butyl | S-OH | 4-F-phenyl | H | F | H | L-fucose | A |
| U | Me | Me | R-(Me)CHOMe | S-OH | 4-F-phenyl | H | F | H | L-fucose | A |

Preparation of a Dimeric IAP Antagonist (Formula 23, Below. Referred to as Compound ["V,"] in Table 2, Below.)

Scheme II

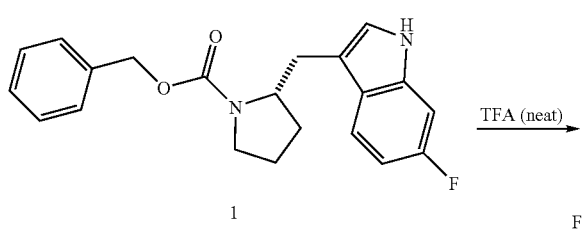

Indoylindoline (14): Fluoroindole 1 (3.55 g, 10.0 mmol) was dissolved in trifluoroacetic acid (15 mL) at 0° C. After 3 h, the solvent was removed in vacuo and the residue was dissolved in EtOAc. The EtOAc solution was washed twice with saturated aqueous NaHCO$_3$ and once with brine. The combined aqueous washes were twice back-extracted with EtOAc and the combined organic extracts were dried over anhydrous Na$_2$SO$_4$, filtered, and concentrated. The crude product was purified by flash silica gel chromatography (hexane/EtOAc, 2:1) to afford 2.48 g of 2 as a foamy solid. Mass spectrum, m/z 705.1 [M+H]+.

Scheme III

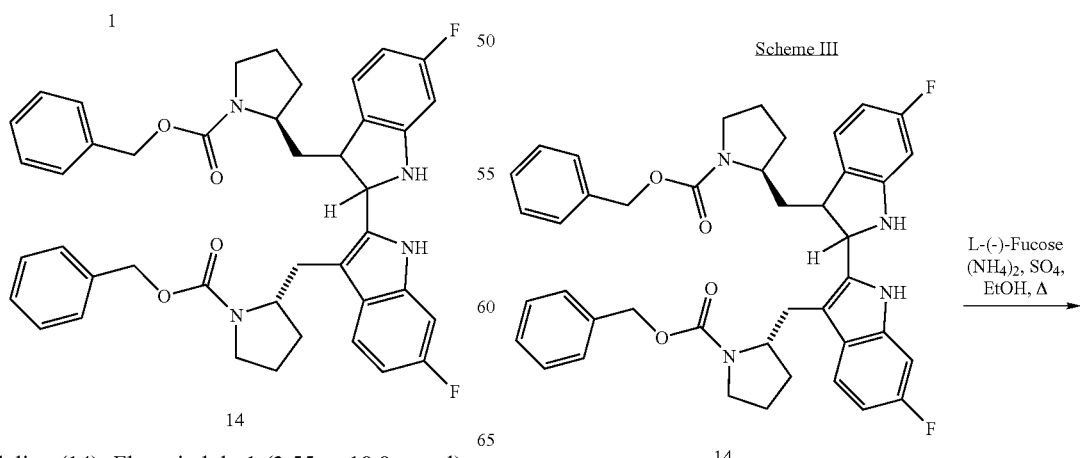

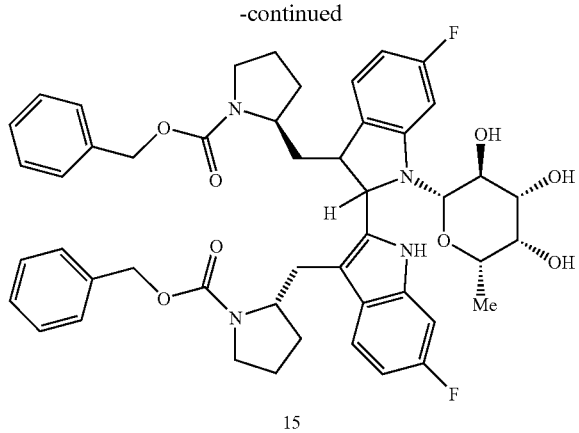

15

Carbohydrate-linked indoylindoline (15): A mixture of 14 (1.24 g, 1.76 mmol), L-(−)-fucose (0.87 g, 5.27 mmol), and powdered (NH$_4$)$_2$SO$_4$ (0.70 g, 5.27 mmol) in absolute EtOH (25 mL) was heated at 75° C. for 24 h. The reaction mixture was absorbed onto silica gel and the product was eluted using 2-5% MeOH in DCM. The fractions containing the two diastereomeric products [TLC analysis: 10% MeOH/DCM, R$_f$(14)=0.8; R$_f$(15)=0.4 and 0.5] were combined and concentrated to provide 0.89 g of 15 which was used directly in the next reaction. Mass spectrum, m/z 851.2 [M+H]+.

Scheme IV

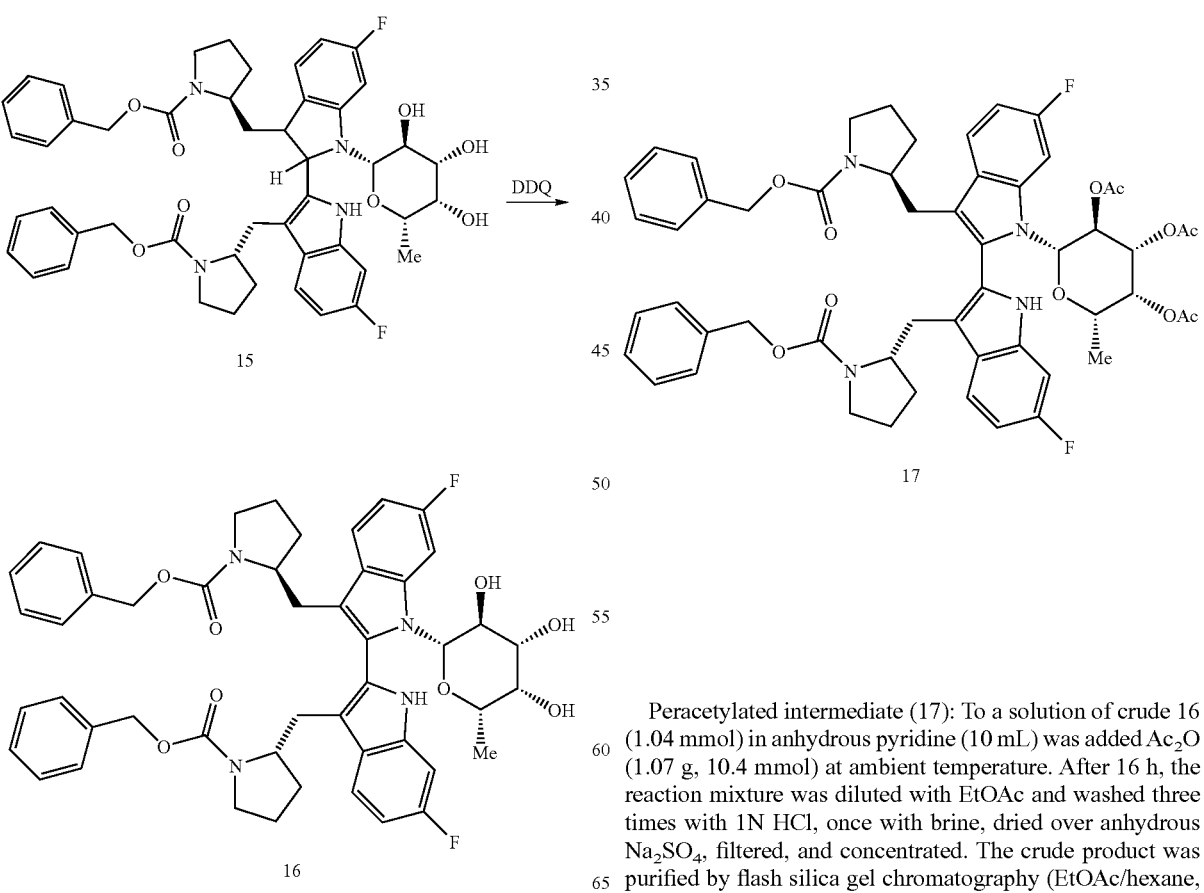

Carbohydrate-linked biindole (16): At ambient temperature, DDQ (0.28 g, 1.25 mmol) was added to a solution of 15 (0.89 g, 1.04 mmol) in 1,4-dioxane (10 mL). After 1 h, the reaction mixture was diluted with EtOAc and washed three times with 0.5 M NaOH, once with brine, dried over anhydrous Na$_2$SO$_4$, filtered, and concentrated to afford crude 16 which was used without further purification. Mass spectrum, m/z 849.2 [M+H]+.

Scheme V

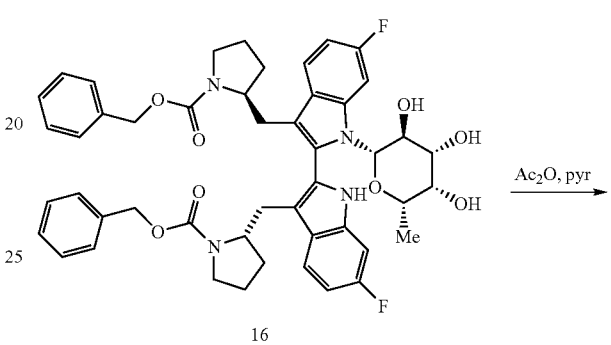

Peracetylated intermediate (17): To a solution of crude 16 (1.04 mmol) in anhydrous pyridine (10 mL) was added Ac$_2$O (1.07 g, 10.4 mmol) at ambient temperature. After 16 h, the reaction mixture was diluted with EtOAc and washed three times with 1N HCl, once with brine, dried over anhydrous Na$_2$SO$_4$, filtered, and concentrated. The crude product was purified by flash silica gel chromatography (EtOAc/hexane, 1:1) to afford 0.82 g of 17 as a solid. Mass spectrum, m/z 975.2 [M]+.

Scheme VI

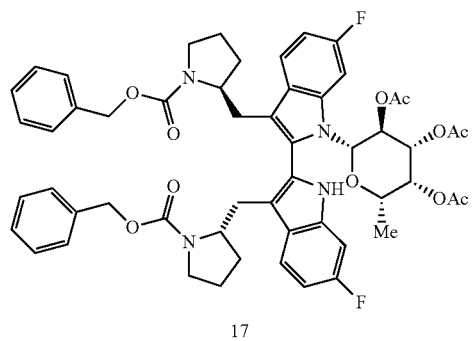

17

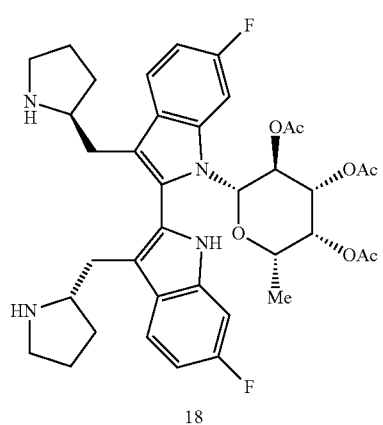

18

Bis-pyrrolidine (18): A mixture of 17 (0.82 g, 0.84 mmol) and 10% Pd-on-C (0.16 g, 20 wt %) in MeOH (20 mL) was placed on a Parr apparatus and shaken under 50 PSI $H_2$ atmosphere. After 2 h, the reaction mixture was filtered using a 0.45μ filter disc which was subsequently washed with excess MeOH. The clarified filtrate was concentrated in vacuo to yield 0.57 g of crude 18 which was used without further purification. Mass spectrum, m/z 354.6 [(M+2H)/2]+.

Scheme VII

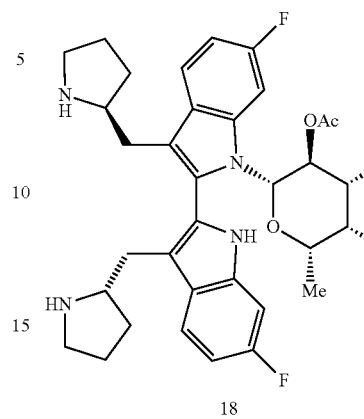

18

19

Cbz-Valine-linked intermediate (19): A solution containing Cbz-L-Val-OH (0.47 g, 1.87 mmol) and HATU (0.67 g, 1.77 mmol) in anhydrous NMP (5 mL) was cooled to 0° C. DIPEA (0.28 g, 2.18 mmol) was added via syringe followed by the addition of 18 (0.57 g, 0.81 mmol) in NMP (5 mL). The reaction mixture was slowly warmed to ambient temperature and the reaction was maintained for ~16 h. The reaction mixture was diluted with diethyl ether and washed successively with 1N HCl water (excess), saturated aqueous $NaHCO_3$, and brine. The organic phase was dried over anhydrous $Na_2SO_4$, filtered, and concentrated. The crude product was purified by flash silica gel chromatography (2% MeOH/DCM) to provide 0.76 g of 19 as a foamy solid. Mass spectrum, m/z 1174.4 (M+H)+.

Scheme VIII

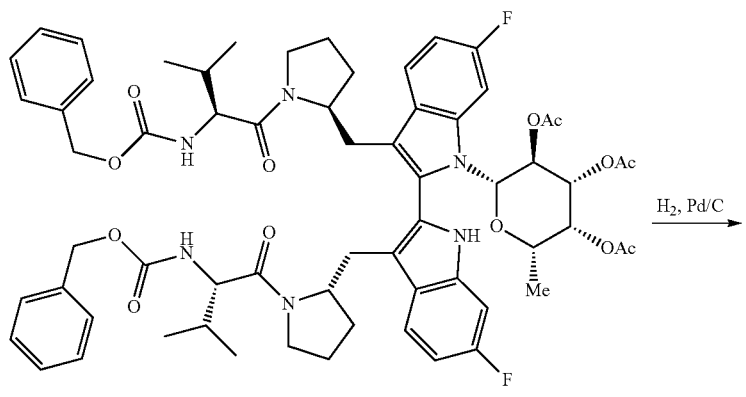

19

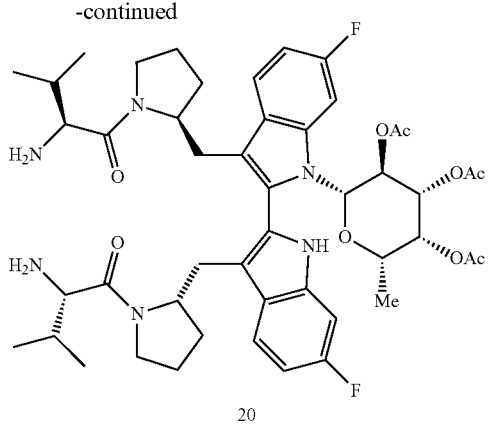

20

Diamine (20): A mixture of 19 (0.76 g, 0.65 mmol) and 10% Pd-on-C (0.15 g, 20 wt t) in MeOH (15 mL) was placed on a Parr apparatus and shaken under 50 PSI $H_2$ atmosphere. After 3 h, the reaction mixture was filtered using a 0.45μ filter disc which was subsequently washed with excess MeOH. The clarified filtrate was concentrated in vacuo to yield 0.57 g of crude 20 which was used without further purification. Mass spectrum, m/z 452.8 [M+2H/2]+.

Scheme IX

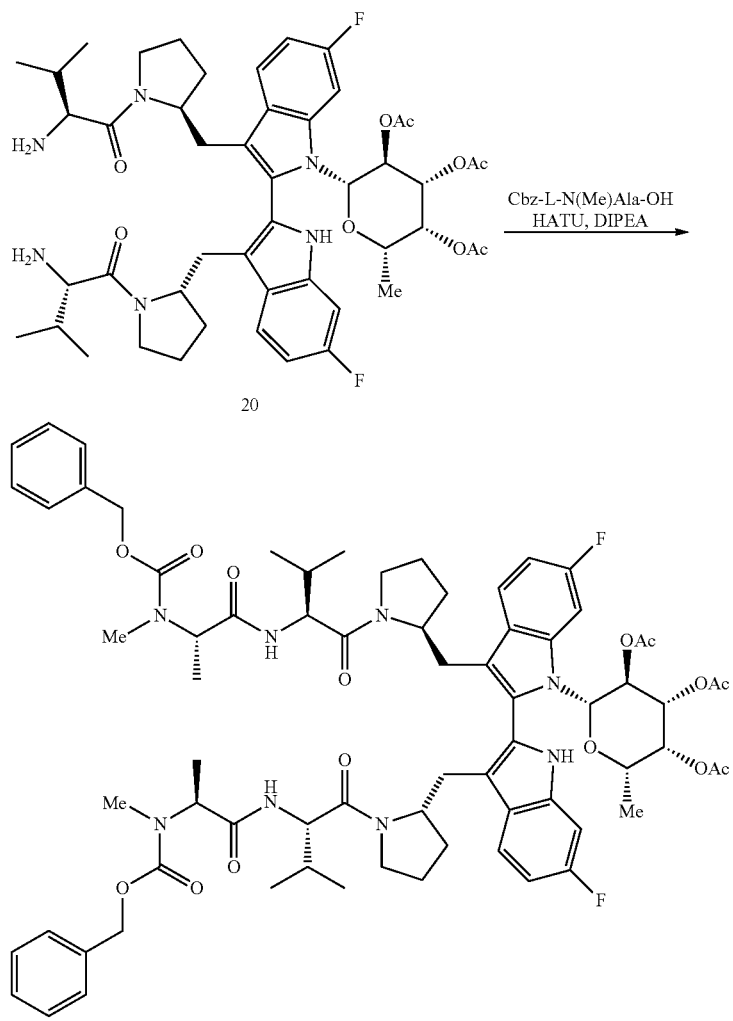

21

Bis-[Cbz-N(Me)Ala] intermediate (21): A solution containing Cbz-L-N(Me)Ala-OH (0.28 g, 1.18 mmol) and HATU (0.43 g, 1.13 mmol) in anhydrous NMP (4 mL) was cooled to 0° C. DIPEA (0.18 g, 1.38 mmol) was added via syringe followed by the addition of 20 (0.47 g, 0.51 mmol) in NMP (4 mL). The reaction mixture was slowly warmed to ambient temperature and the reaction was maintained for about 16 h. The reaction mixture was diluted with diethyl ether and washed successively with 1N HCl, water (excess), saturated aqueous NaHCO$_3$, and brine. The organic phase was dried over anhydrous Na$_2$SO$_4$, filtered, and concentrated to provide 0.69 g of crude 21 as a solid. Mass spectrum, m/z 1343.4 (M)+.

Scheme X

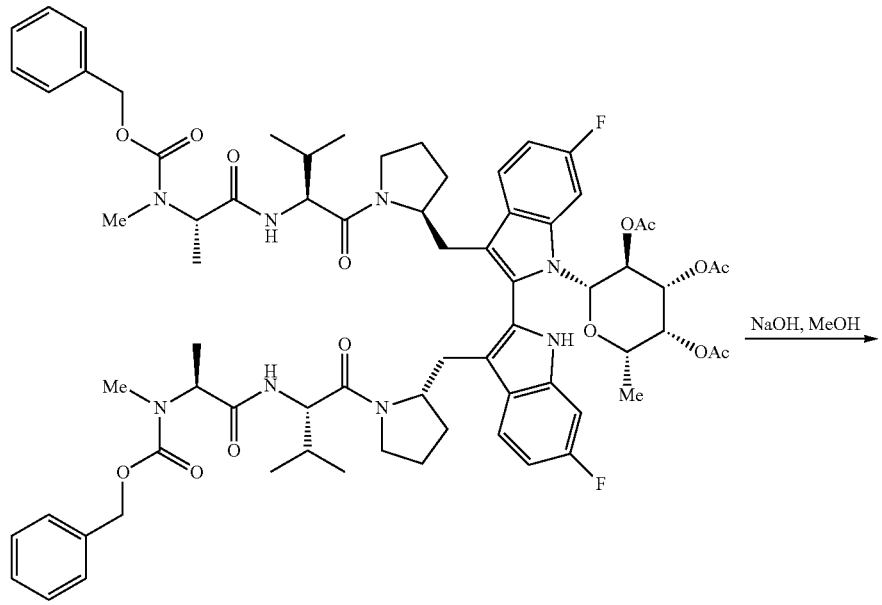

21

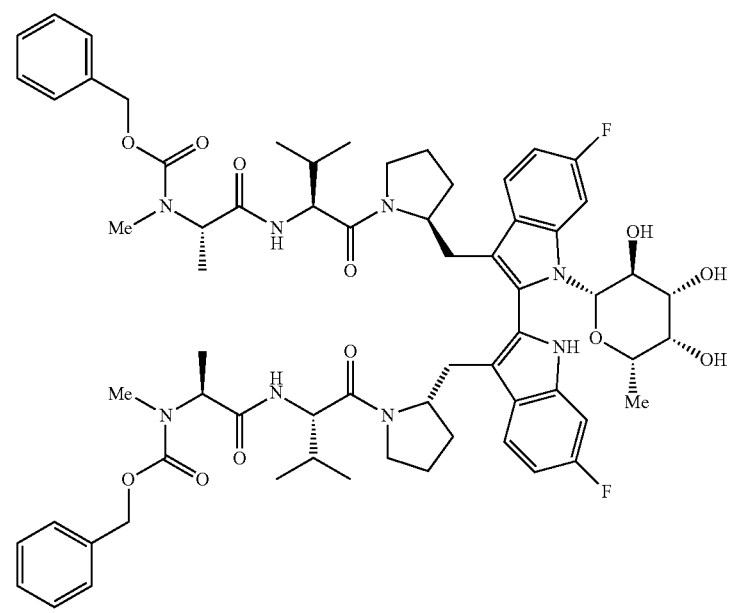

22

Hydroxylated pyranose (22): To a solution of 21 (0.69 g, 0.51 mmol) in MeOH (20 mL) was added 1N NaOH (1.7 mL, 1.7 mmol) at 0° C. After 2 h, the reaction mixture was diluted with saturated aqueous NH₄Cl and brine and the product was extracted with EtOAc. The combined organic extracts were dried over anhydrous Na₂SO₄, filtered, and concentrated to afford 0.62 g of crude 22 which was used without further purification.

Scheme XI

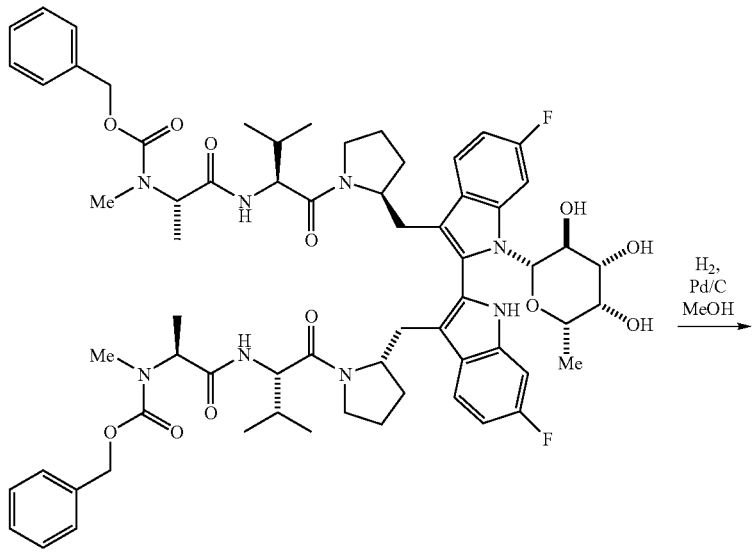

22

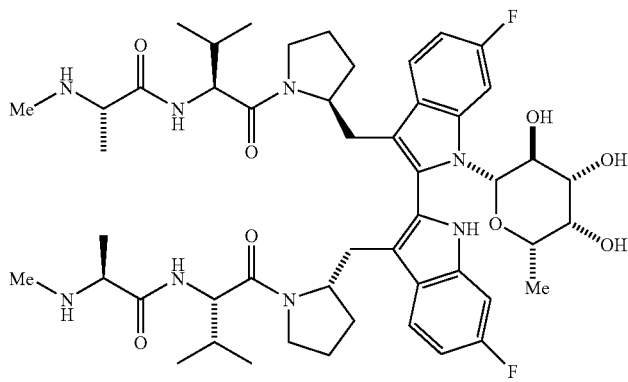

23

Dimeric IAP Antagonist (23): A mixture of 22 (0.62 g, 0.51 mmol) and 10% Pd-on-C (0.15 g, 20 wt %) in MeOH (20 mL) was placed on a Parr apparatus and shaken under 50 PSI H₂ atmosphere. After 4 h, the reaction mixture was filtered using a 0.45µ filter disc which was subsequently washed with excess MeOH. The clarified filtrate was concentrated in vacuo. The crude product was purified by reverse-phase HPLC (2" Dynamax C18 column; Flow rate: 40 mL/min; Detector: 254 nm; Method: 10-50% ACN/water containing 0.1% HOAc over 25 min). The product-containing fractions were combined and concentrated in vacuo to remove excess ACN then lyophilized to dryness to provide 0.23 g of 23.2HOAc as a flocculent white solid. Mass spectrum, m/z 475.8 [(M+2H)/2]+.

TABLE 2

Binding of Dimeric IAP Antagonists to XIAP BIR3

| Compound | R1 | R2 | R3 | R18 | R13 | R12 | R10 | $K_D$, µM |
|---|---|---|---|---|---|---|---|---|
| V | Me | Me | iPr | H | H | F | L-fucose | A |
| W | H | H | iPr | H | H | F | L-fucose | B |
| X | H | H | iPr | H | H | F | D-xylose | C |
| Y | Me | Me | iPr | H | H | F | D-xylose | A |
| Z | Me | Me | R-(Me)CHOH | H | F | H | D-galactose | B |
| AA | Me | Me | iPr | H | F | H | D-galactose | A |
| BB | Me | Me | R-(Me)CHOH | H | F | H | D-glucose | |
| CC | Me | Me | iPr | H | F | H | D-glucose | A |
| DD | Me | Me | iPr | H | F | H | L-fucose | A |
| EE | Me | Me | R-(Me)CHOMe | H | H | F | L-fucose | A |
| FF | Me | Me | R-(Me)CHOMe | S-OH | H | F | L-fucose | A |
| GG | Me | Me | R-(Me)CHOH | S-OH | H | F | L-fucose | A |

Preparation of Smac Mimetic (Piperidine-Substituted Monomer, Formula 30, Below. Referred to as Compound "[HH]" in Table 3, Below.)

Scheme XII

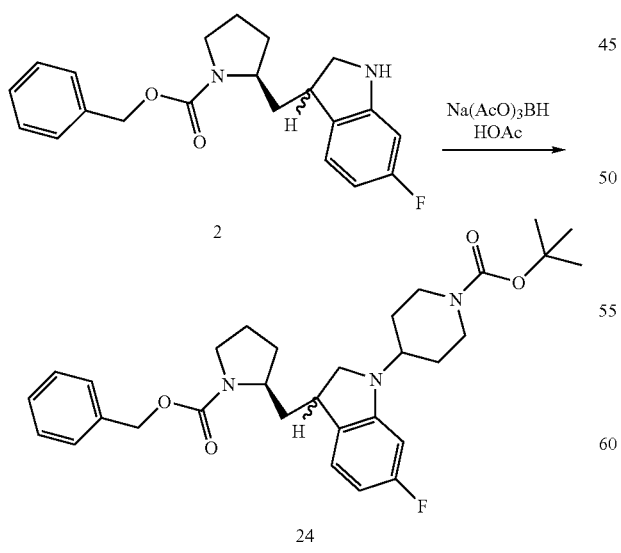

N-Alkylated indoline (24): To a solution containing indoline 2 (4.6 g, 13.0 mmol) in glacial HOAc (40 mL) was added 4-BOC-piperidone (2.85 g, 14.3 mmol). After 10 min, Na(AcO)₃BH (4.13 g, 19.5 mmol) was added in small portions over 40 min maintaining the temperature below 30° C. After 1 h, the reaction mixture was diluted with water and EtOAc. Aqueous NaOH (1M) was added and the layers were separated. The organic phase was washed with 1M NaOH until pH=12, then washed with brine, dried over anhydrous Na₂SO₄, filtered and concentrated to afford crude 24 (quant.) as an oil which was used without further purification. ¹H NMR (300 MHz, CDCl₃): 7.35-7.35 (m, 5H), 6.92-6.78 (m, 1H), 6.25-6.18 (m, 1H), 6.09-6.06 (m, 1H), 5.12-5.09 (m, 2H), 4.22 (br, 2H), 3.87-3.70 (m, 1H), 3.55-3.41 (m, 3H), 3.21-3.02 (m, 3H), 2.75-2.72 (br, 2H), 1.98-1.60 (m, 8H), 1.49-1.46 (m, 9H) ppm.

Scheme XIII

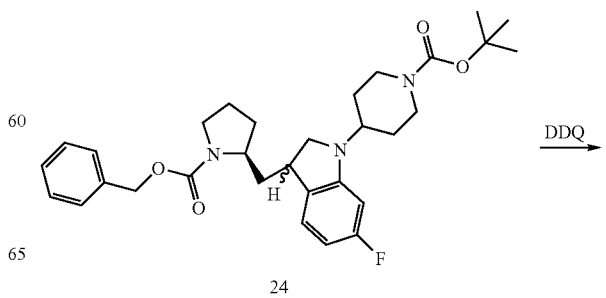

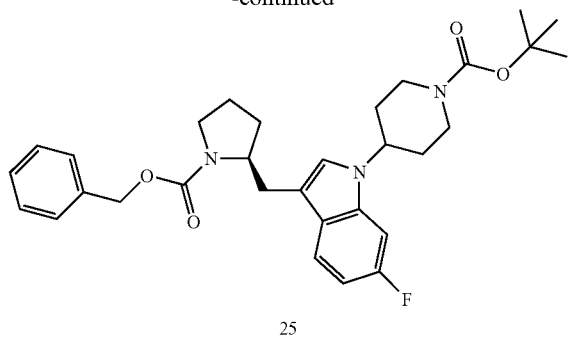

25

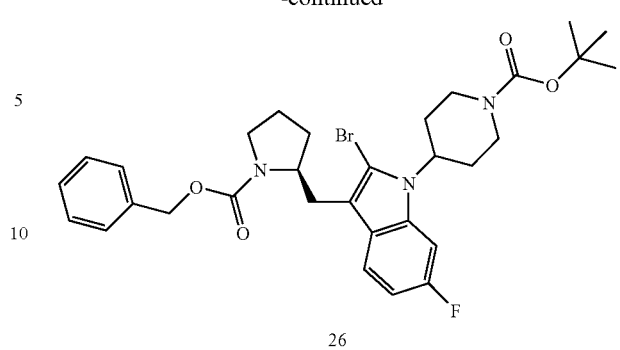

26

Indole (25): To a solution containing crude indoline 24 (7.46 g, 13 mmol) in anhydrous 1,4-dioxane (75 mL) was added 2,3-dichloro-5,6-dicyanobenzoquinone (3.78 g, 16.6 mmol) in small portions. After 2 h, the reaction mixture was diluted with EtOAc, and filtered through Celite®. The pad was washed with EtOAc and the filtrate was washed with saturated aqueous $NaHCO_3$, brine, dried over anhydrous $Na_2SO_4$, filtered and concentrated. The product was purified by flash silica gel column chromatography [2:1 hexane/EtOAc] to afford 3.81 g (51%) indole 25. $^1$H NMR (300 MHz, $CDCl_3$): ~1:1 mixture of carbamate rotamers, 7.71-7.67 (m, 0.5H), 7.43-7.38 (m, 5H), 7.18-7.14 (m, 0.5H), 6.99-6.82 (m, 2.5H), 6.61 (t, J=2.9 Hz, 0.5H), 5.19 (s, 2H), 4.30-4.08 (m, 2H), 3.74-3.70 (m, 0.5H), 3.46-3.39 (m, 2H), 3.29 (d, J=4.3 Hz, 0.5H), 3.13 (d, J=4.4 Hz, 0.5H), 2.88 (br m, 2H), 2.72-2.54 (m, 1H), 2.44 (t, J=2.0 Hz, 0.5H), 2.00 (br, 1H), 1.85-1.67 (m, 6H), 1.49 (s, 9H) ppm.

Scheme XIV

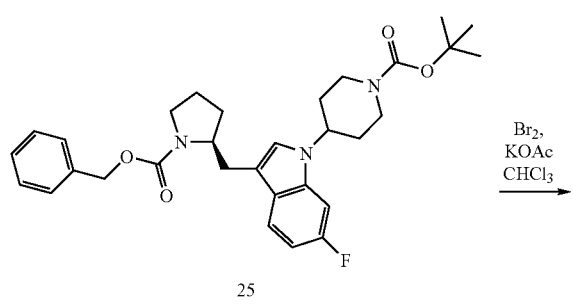

25

→ $Br_2$, KOAc $CHCl_3$

Bromoindole (26): A solution containing indole 25 (3.81 g, 7.12 mmol) in $CHCl_3$ (100 mL) was cooled to 0° C. and KOAc (2.1 g, 21.4 mmol) was added followed by the dropwise addition of a solution of bromine (1.36 g, 8.54 mmol) in $CHCl_3$ (5 mL). After 1 h, the reaction mixture was diluted with brine and DCM. The layers were separated and the organic phase was washed with saturated aqueous $Na_2S_2O_4$, brine, dried over anhydrous $Na_2SO_4$, filtered and concentrated. The product was purified by flash silica gel column chromatography [2:1 hexane/EtOAc] to afford 2.78 g (64%) of bromoindole 26 as a yellow solid. $^1$H NMR (300 MHz, $CDCl_3$): ~1:1 mixture of carbamate rotamers, 7.76-7.71 (m, 0.5H), 7.45-7.32 (m, 5H), 7.13-7.06 (m, 1.5H), 6.86 (t, J=2.6 Hz, 0.5H), 6.56 (t, J=2.9 Hz), 0.5H), 5.22-5.18 (m, 2H), 4.59-4.55 (br, 1H), 4.32-4.23 (br, 2H), 3.59-3.34 (m, 2H), 3.29 (dd, J=4.6, 1.0 Hz, 0.5H), 3.07 (dd, J=4.6, 1.2 Hz, 0.5H), 2.86 (br, 2H), 2.74-2.61 (m, 1H), 2.41 (br, 2H), 1.76-1.65 (m, 5H), 1.52 (s, 9H) ppm.

Scheme XV

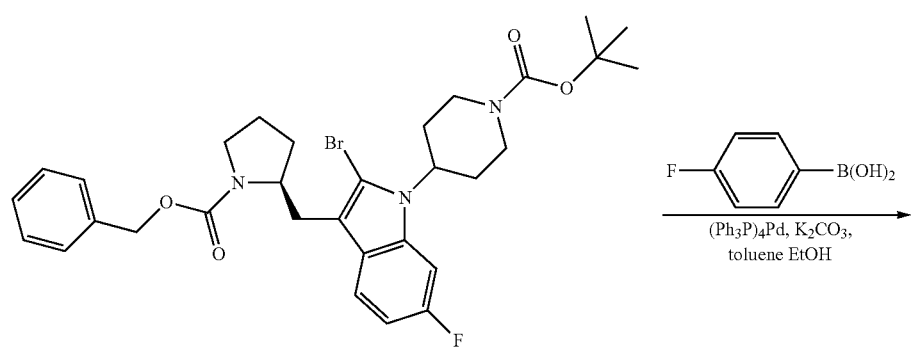

26 → $(Ph_3P)_4Pd$, $K_2CO_3$, toluene EtOH

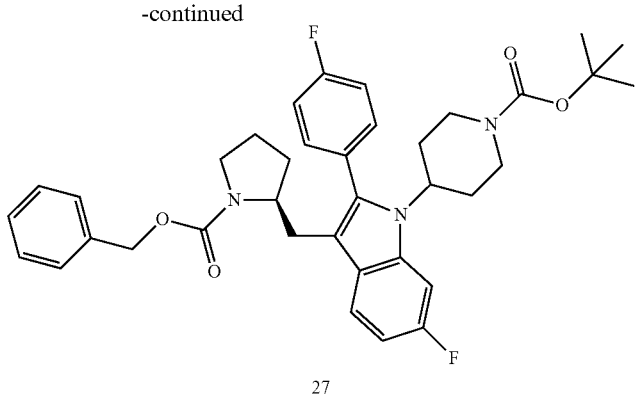

27

2-Substituted indole (27): A mixture containing bromoindole 26 (2.78 g, 4.52 mmol), K₂CO₃ (2.19 g, 11.3 mmol) and 4-fluorobenzeneboronic acid (0.82 g, 5.88 mmol) in toluene (21 mL) and EtOH (7 mL) was degassed under vacuum. After the addition of (Ph₃P)₄Pd(0) (0.26 g, 0.23 mmol), the mixture was degassed again and placed in an oil bath preheated at 90° C. After 2.5 h, the reaction mixture was cooled to ambient temperature and diluted with EtOAc, washed with 1M HCl, brine, dried over anhydrous Na₂SO₄, filtered and concentrated. The product was purified by flash silica gel column chromatography [2:1 hexane/EtOAc] to afford 2.46 g (86%) of indole 27 as a yellow solid. ¹H NMR (300 MHz, CDCl₃): ~1:1 mixture of carbamate rotamers, 7.88-7.84 (m, 0.5H), 7.38-7.14 (m, 10.5H), 6.94-6.87 (m, 0.5H), 6.64-6.59 (m, 0.5H), 5.21-4.97 (m, 2H), 4.19-3.95 (m, 2H), 3.30-3.25 (m, 2H), 3.03 (dd, J=4.6 Hz, 1.3 Hz, 0.5H), 2.82 (br, 0.5H), 2.61-2.57 (m, 2H), 2.44-2.28 (m, 4H), 1.83-1.74 (m, 1H), 1.62-1.58 (m, 2H), 1.52-1.46 (m, 9H), 1.41-1.37 (m, 2H) ppm.

Scheme XVI

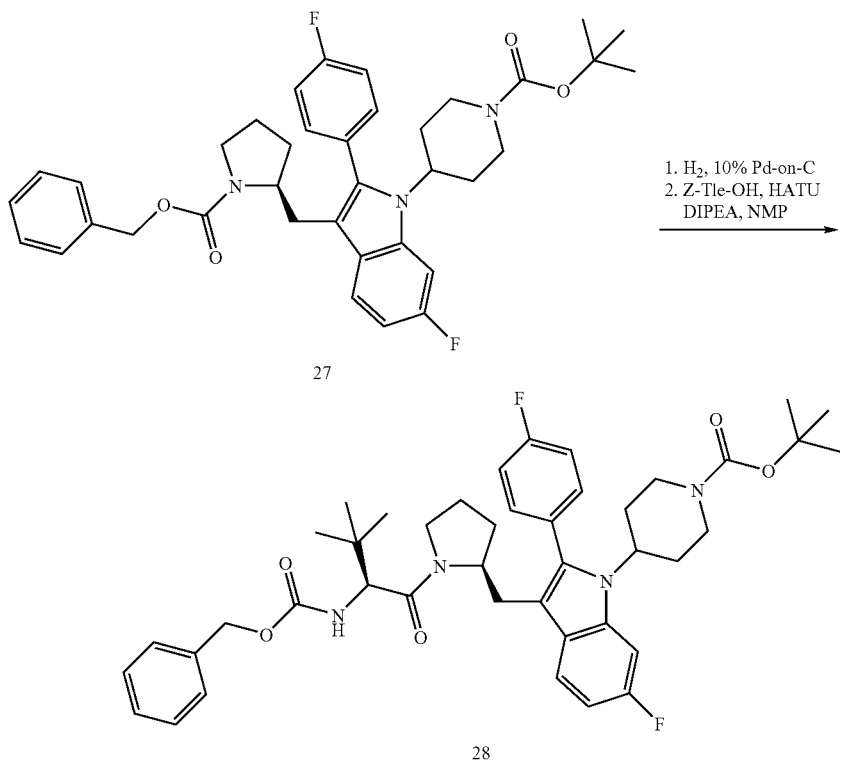

Cbz-protected amine (28): A mixture containing indole 27 (2.46 g, 3.91 mmol) and 10% Pd/C (480 mg, 20 wt %) in MeOH (25 mL) was shaken under a hydrogen atmosphere (50 psi) using a Parr apparatus. After 5 h, the reaction mixture was filtered through Celite® and the pad was washed with MeOH. The filtrate was concentrated and the residue was purified by flash silica gel column chromatography [2% to 20% MeOH/DCM] to afford 550 mg of intermediate amine. Mass spectrum, m/z=495.6 [M+].

A solution containing Cbz-L-tert-leucine dicyclohexylamine salt (644 mg, 1.44 mmol) and HATU (548 mg, 1.44 mmol) in NMP (7 mL) was cooled to 0° C. and DIPEA (0.29 g, 2.22 mmol) was added. After 15 min, a solution containing the previously-prepared intermediate amine (550 mg, 1.11 mmol) in NMP (5 mL) was added. The reaction mixture was stirred to ambient temperature. After 16 h, the reaction mixture was diluted with diethyl ether, washed with 1M HCl, water, saturated aqueous NaHCO$_3$, water, and brine. The organic phase was dried over anhydrous Na$_2$SO$_4$, filtered and concentrated. The product was purified by flash silica gel column chromatography [1:1 hexane/EtOAc] to afford 111 mg (13%) of amide 28 as a foam. $^1$H NMR (300 MHz, CDCl$_3$): 8.03-7.99 (m, 1H), 7.34-7.12 (m, 10H), 7.02-6.91 (m, 1H), 5.62-5.58 (m, 1H), 5.16-5.02 (m, 2H), 4.49-4.47 (m, 1H), 4.32-4.08 (m, 2H), 3.99-3.94 (m, 1H), 3.61-3.43 (m, 1H), 3.31-3.27 (m, 1H), 2.59 (br, 1H), 2.41-2.17 (m, 2H), 1.88-1.84 (m, 1H), 1.57 (m, 5H), 1.49 (s, 9H), 1.31-1.19 (m, 4H), 1.01-0.95 (m, 9H) ppm. Mass spectrum, m/z 743.7 [M+H]+.

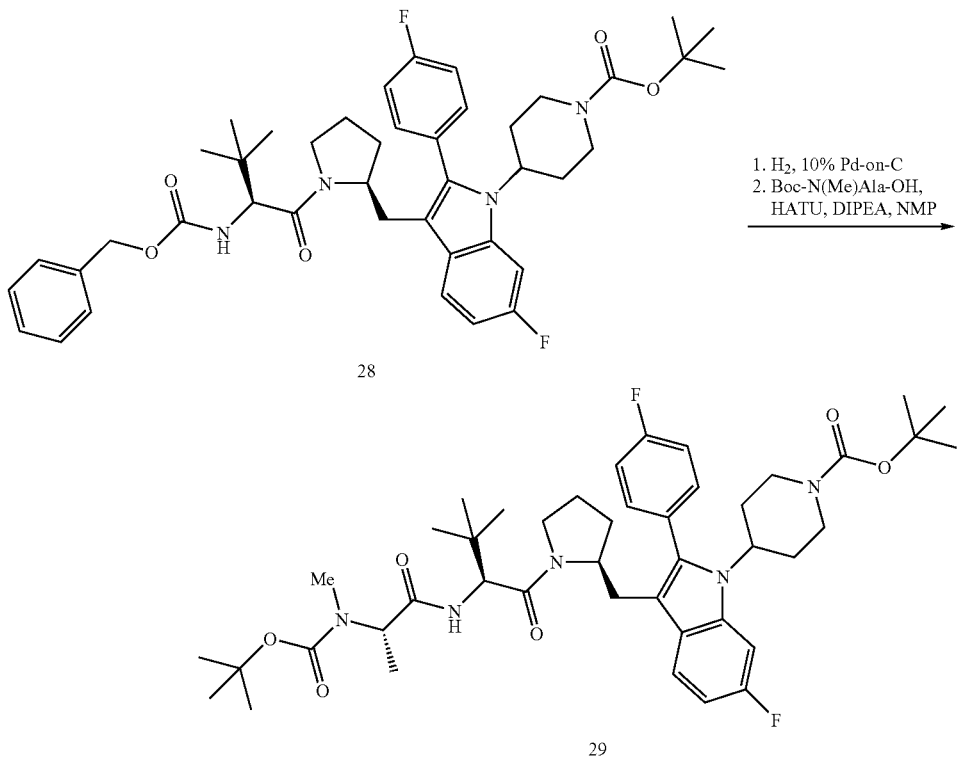

Boc-protected peptide (29): A mixture of amide 28 (110 mg, 0.15 mmol) and 10% Pd/C (30 mg, 20 wt %) in MeOH (10 mL) was shaken under a hydrogen atmosphere at (45 psi) using a Parr apparatus. After 2 h, the reaction mixture was filtered through a 0.45 mM filter disc which was rinsed with excess MeOH. The filtrate was concentrated to afford 69 mg of intermediate amine. Mass spectrum, m/z=608.7 [M+].

A solution containing Boc-N(Me)Ala-OH (35 mg, 0.17 mmol) and HATU (65 mg, 0.17 mmol) in NMP (2 mL) was cooled to 0° C. and DIPEA (0.029 g, 0.23 mmol) was added. After 15 min, a solution containing the previously-prepared intermediate amine (69 mg, 0.11 mmol) in NMP (3 mL) was added. The reaction was stirred to ambient temperature over 2 h then diluted with diethyl ether and washed successively with 1M HCl, water, saturated aqueous NaHCO$_3$, water, and brine. The organic phase was dried over anhydrous Na$_2$SO$_4$, filtered and concentrated to afford 105 mg of crude Boc-peptide 29 as a foam which was used directly without further purification. Mass spectrum, m/z=793.9 [M+].

Scheme XVIII

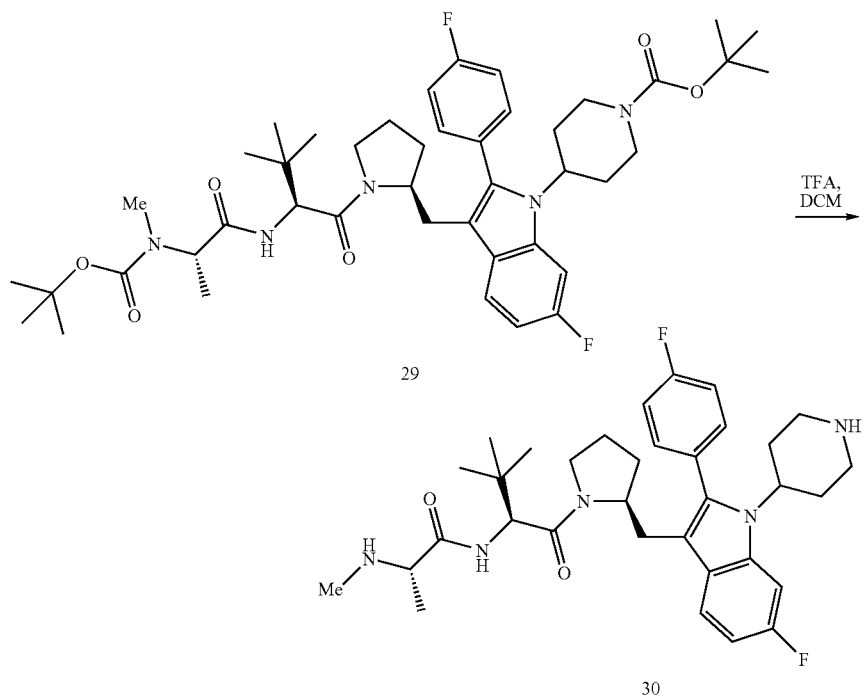

Dipeptide (30): To a solution containing Boc-peptide 29 (100 mg, 0.13 mmol) in DCM (10 mL) was added TFA 12 mL) at 0° C. After 1 h, the solvent was removed in vacuo and the residue was dissolved in EtOAc, washed successively with saturated aqueous NaHCO$_3$, brine, dried over anhydrous Na$_2$SO$_4$, filtered and concentrated. The crude product was purified by C18 reverse-phase HPLC [10% to 70% ACN/water containing 0.1% v/v HOAc]. Lyophilization of the product-containing fractions afforded 28 mg (38%) of dipeptide 30 as a white solid. $^1$H NMR (300 MHz, CDCl$_3$): 8.03-7.98 (m, 1H), 7.86-7.69 (m, 2H), 7.59-7.46 (m, 1H), 7.28-7.17 (m, 5H), 7.05-6.91 (m, 1H), 4.94-4.77 (br m, 5H), 4.59 (d, J=3.2 Hz, 1H), 4.49-4.46 (m, 1H), 3.97 (br m, 2H), 3.72-3.20 (m, 3H), 2.13-3.05 (m, 1H), 2.89-2.62 (m, 3H), 2.40-2.18 (m, 2H), 2.08-1.94 (m, 3H), 1.08-0.95 (m, 10H) ppm. Mass spectrum, m/z=593.7 [M+].

TABLE 3

Binding of Monomeric IAP Antagonists to XIAP BIR3.

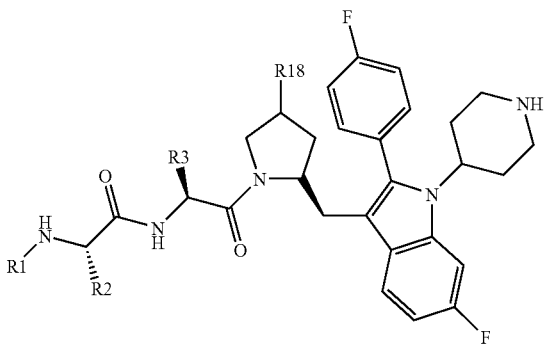

| Compound | R1 | R2 | R3 | R18 | K$_D$, μM |
|---|---|---|---|---|---|
| HH | Me | Me | tBu | H | A |
| II | Me | Me | R-(Me)CHOMe | H | A |

TABLE 3-continued

Binding of Monomeric IAP Antagonists to XIAP BIR3.

| Compound | R1 | R2 | R3 | R18 | K$_D$, μM |
|---|---|---|---|---|---|
| JJ | Me | Et | R-(Me)CHOMe | H | A |
| KK | Me | cyclopropyl | R-(Me)CHOMe | H | B |
| LL | Me | Me | tBu | S-OH | A |
| MM | Et | Me | tBu | S-OH | B |
| NN | Me | CH$_2$OH | tBu | S-OH | B |
| OO | Me | cyclopropyl | tBu | S-OH | D |
| PP | Me | Me | R-(Me)CHOMe | S-OH | A |
| QQ | Et | Me | R-(Me)CHOMe | S-OH | A |
| RR | Me | Et | R-(Me)CHOMe | S-OH | A |
| SS | Me | cyclopropyl | R-(Me)CHOMe | S-OH | B |

In mammalian cells, activation of the caspases is achieved through at least two independent mechanisms which are initiated by distinct caspases, but result in the activation of common executioner (effector) caspases. In addition to the cytochrome c activated mechanism (sometimes referred to as the 'intrinsic death pathway') is a mechanism by which the caspase cascade is activated via activation of a death receptor located on the cell membrane (sometimes referred to as the 'extrinsic death pathway'). Examples of death receptors include CD-95 and TNF-R1 (as well as other members of the TNF group of cytokine receptors). The corresponding ligands are CD-95L and TNF-alpha, respectfully. Binding of pro-caspase-8 to the death receptor induces auto-activation wherein the inhibitory pro-domain of pro-caspase-8 is cleaved and removed. Caspase-8 is released from the receptor and can then activate effector caspases (caspase-3, -6, -7), and, as in the caspase-9 initiated pathway, the result is the proteolytic cleavage of cellular targets by the effector caspases and the induction of apoptosis.

The present invention is directed generally to Smac peptidomimetics and the uses of Smac peptidomimetics. In one embodiment the Smac peptidomimetics act as chemopotentiating agents. The term "chemopotentiating agent" refers to an agent that acts to increase the sensitivity of an organism, tissue, or cell to a chemical compound, or treatment namely "chemotherapeutic agents" or "chemo drugs" or radiation treatment. One embodiment of the invention is the therapeutic composition of a Smac peptidomimetic. A further embodiment of the invention is the therapeutic composition of a Smac peptidomimetic, which can act as a chemopotentiating agent (herein referred to as Smac mimetic), and a biological or chemotherapeutic agent or radiation. Another embodiment of the invention is a method of inhibiting tumor growth in vivo by administering a Smac peptidomimetic. Another embodiment of the invention is a method of inhibiting tumor growth in vivo by administering a Smac mimetic and a biologic or chemotherapeutic agent or chemoradiation. Another embodiment of the invention is a method of treating a patient with a cancer by administering Smac mimetics of the present invention alone or in combination with a chemotherapeutic agent or chemoradiation.

In an embodiment of the present invention, the cells are in situ, in an individual, and the contacting step is effected by administering a pharmaceutical composition comprising a therapeutically effective amount of the Smac mimetic wherein the individual may be subject to concurrent or antecedent radiation or chemotherapy for treatment of a neoproliferative pathology. The pathogenic cells are of a tumor such as, but not limited to, bladder cancer, breast cancer, prostate cancer, lung cancer, pancreatic cancer, gastric cancer, colon cancer, ovarian cancer, renal cancer, hepatoma, melanoma, lymphoma, sarcoma, and combinations thereof.

As described in U.S. Pat. No. 7,244,851, IAP antagonists can be used for the treatment of all cancer types which fail to undergo apoptosis. Examples of such cancer types include neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erthematosus or rheumatoid arthritis.

In an embodiment the pathogenic cells are those of any autoimmune disease or diseases which are resistant to apoptosis due to the expression of IAPs or members of the Bcl-2 family, Examples of such autoimmune diseases are collagen diseases such as rheumatoid arthritis, systemic lupus erythematosus, Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotony, Guillain-Barré syndrome (Müller-Fischer syndrome) stiff-man syndrome, cerebellar degeneration, ataxia, opsoklonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, Malaria and Chagas disease.

The subject compositions encompass pharmaceutical compositions comprising a therapeutically effective amount of a Smac mimetic in dosage form and a pharmaceutically acceptable carrier, wherein the Smac mimetic inhibits the activity of an Inhibitor of Apoptosis protein (IAP), thus promoting apoptosis. Another embodiment of the present invention are compositions comprising a therapeutically effective amount of a Smac mimetic in dosage form and a pharmaceutically acceptable carrier, in combination with a chemotherapeutic and/or radiotherapy, wherein the Smac mimetic inhibits the activity of an Inhibitor of Apoptosis protein (IAP), thus promoting apoptosis and enhancing the effectiveness of the chemotherapeutic and/or radiotherapy.

In an embodiment of the invention a therapeutic composition for promoting apoptosis can be a therapeutically effective amount of a Smac peptidomimetic which binds to at least one IAP. In one embodiment the IAP can be XIAP. In another embodiment the IAP can be ML-IAP. In another embodiment the IAP can cIAP-1 or cIAP-2. In a further embodiment the IAP can be multiple IAP types.

Embodiments of the invention also include a method of treating a patient with a condition in need thereof wherein administration of a therapeutically effective amount of a Smac peptidomimetic is delivered to the patient, and the Smac peptidomimetic binds to at least one IAP. In one embodiment the IAP can be XIAP. In another embodiment the IAP can be ML-IAP. In another embodiment the IAP can cIAP-1 or cIAP-2. In a further embodiment the SAP can be multiple IAP types. The method may further include the concurrent administration of another chemotherapeutic agent. The chemotherapeutic agent can be, but is not limited to, alkylating agents, antimetabolites, anti-tumor antibiotics, taxanes, hormonal agents, monoclonal antibodies, glucocorticoids, mitotic inhibitors, topoisomerase I inhibitors, topoisomerase II inhibitors, immunomodulating agents, cellular growth factors, cytokines, and nonsteroidal anti-inflammatory compounds.

Administration of Smac peptidomimetics The Smac peptidomimetics can be administered in effective amounts. An effective amount is that amount of a preparation that alone, or together with further doses, produces the desired response. This may involve only slowing the progression of the disease temporarily, although preferably, it involves halting the progression of the disease permanently or delaying the onset of or preventing the disease or condition from occurring. This can be monitored by routine methods. Generally, doses of active compounds would be from about 0.01 mg/kg per day to 1000 mg/kg per day. It is expected that doses ranging from 50-500 mg/kg will be suitable, preferably intravenously, intramuscularly, or intradermally, and in one or several administrations per day. The administration of the Smac peptidomimetic can occur simultaneous with, subsequent to, or prior to chemotherapy or radiation so long as the chemotherapeutic agent or radiation sensitizes the system to the Smac peptidomimetic.

In general, routine experimentation in clinical trials will determine specific ranges for optimal therapeutic effect for each therapeutic agent and each administrative protocol, and administration to specific patients will be adjusted to within effective and safe ranges depending on the patient condition and responsiveness to initial administrations. However, the ultimate administration protocol will be regulated according to the judgment of the attending clinician considering such factors as age, condition and size of the patient, the Smac peptidomimetic potencies, the duration of the treatment and the severity of the disease being treated. For example, a dosage regimen of the Smac peptidomimetic can be oral administration of from 1 mg to 2000 mg/day, preferably 1 to 1000 mg/day, more preferably 50 to 600 mg/day, in two to four (preferably two) divided doses, to reduce tumor growth. Intermittent therapy (e.g., one week out of three weeks or three out of four weeks) may also be used.

In the event that a response in a subject is insufficient at the initial doses applied, higher doses (or effectively higher doses by a different, more localized delivery route) may be employed to the extent that the patient tolerance permits. Multiple doses per day are contemplated to achieve appropriate systemic levels of compounds. Generally, a maximum dose is used, that is, the highest safe dose according to sound medical judgment. Those of ordinary skill in the art will understand, however, that a patient may insist upon a lower dose or tolerable dose for medical reasons, psychological reasons or for virtually any other reason.

Embodiments of the invention also include a method of treating a patient with cancer by promoting apoptosis wherein administration of a therapeutically effective amount of a Smac peptidomimetic, and the Smac peptidomimetic binds to at least one IAP. In one embodiment the IAP can be XIAP. In another embodiment the IAP can be ML-IAP. In another embodiment the IAP can cIAP-1 or cIAP-2. In a further embodiment the IAP can be multiple IAP types. The method may further include concurrent administration of a chemotherapeutic agent. The chemotherapeutic agent can be, but is not limited to, alkylating agents, antimetabolites, anti-tumor antibiotics, taxanes, hormonal agents, monoclonal antibodies, glucocorticoids, mitotic inhibitors, topoisomerase I inhibitors, topoisomerase II inhibitors, immunomodulating agents, cellular growth factors, cytokines, and nonsteroidal anti-inflammatory compounds.

Routes of administration A variety of administration routes are available. The particular mode selected will depend, of course, upon the particular chemotherapeutic drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include, but are not limited to, oral, rectal, topical, nasal, intradermal, inhalation, intra-peritoneal, or parenteral routes. The term "parenteral" includes subcutaneous, intravenous, intramuscular, or infusion. Intravenous or intramuscular routes are particularly suitable for purposes of the present invention.

In one aspect of the invention, a Smac peptidomimetic as described herein, with or without additional biological or chemotherapeutic agents or radiotherapy, does not adversely affect normal tissues, while sensitizing tumor cells to the additional chemotherapeutic/radiation protocols. While not wishing to be bound by theory, it would appear that because of this tumor specific induced apoptosis, marked and adverse side effects such as inappropriate vasodilation or shock are minimized. Preferably, the composition or method is designed to allow sensitization of the cell or tumor to the chemotherapeutic or radiation therapy by administering at least a portion of the Smac peptidomimetic prior to chemotherapeutic or radiation therapy. The radiation therapy, and/or inclusion of chemotherapeutic agents, may be included as part of the therapeutic regimen to further potentiate the tumor cell killing by the Smac peptidomimetic.

Pharmaceutical compositions In one embodiment of the invention, an additional chemotherapeutic agent (infra) or radiation may be added prior to, along with, or following the Smac peptidomimetic. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The delivery systems of the invention are designed to include time-released, delayed release or sustained release delivery systems such that the delivering of the Smac peptidomimetic occurs prior to, and with sufficient time, to cause sensitization of the site to be treated. A Smac peptidomimetic may be used in conjunction with radiation and/or additional anti-cancer chemical agents (infra). Such systems can avoid repeated administrations of the Smac peptidomimetic compound, increasing convenience to the subject and the physician, and may be particularly suitable for certain compositions of the present invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active compound is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be desirable. Long-term release, are used herein, means that the implant is constructed and arranged to deliver therapeutic levels of the active ingredient for at least 30 days, and preferably 60 days. Long-term sustained release implants are well-known to those of ordinary skill in the art and include some of the release systems described above.

The pharmaceutical compositions may conveniently be presented in unit dosage form and may be prepared by any of the methods well known in the art of pharmacy. All methods include the step of bringing the active agent into association with a carrier that constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for parenteral administration conveniently comprise a sterile aqueous preparation of a chemopotentiating agent (e.g. Smac peptidomimetic), which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa. which is incorporated herein in its entirety by reference thereto.

Additional chemotherapeutic agents Chemotherapeutic agents suitable, include but are not limited to the chemotherapeutic agents described in "Modern Pharmacology with Clinical Applications", Sixth Edition, Craig & Stitzel, Chpt. 56, pg 639-656 (2004), herein incorporated by reference. This reference describes chemotherapeutic drugs to include alkylating agents, antimetabolites, anti-tumor antibiotics, plant-derived products such as taxanes, enzymes, hormonal agents such as glucocorticoids, miscellaneous agents such as cisplatin, monoclonal antibodies, immunomodulating agents such as interferons, and cellular growth factors. Other suitable classifications for chemotherapeutic agents include mitotic inhibitors and nonsteroidal anti-estrogenic analogs. Other suitable chemotherapeutic agents include topoisomerase I and II inhibitors and kinase inhibitors.

Specific examples of suitable biological and chemotherapeutic agents include, but are not limited to, cisplatin, carmustine (BCNU), 5-fluorouracil (5-FU), cytarabine (Ara-C), gemcitabine, methotrexate, daunorubicin, doxorubicin, dexamethasone, topotecan, etoposide, paclitaxel, vincristine, tamoxifen, TNF-alpha, TRAIL, interferon (in both its alpha and beta forms), thalidomide, and melphalan. Other specific examples of suitable chemotherapeutic agents include nitrogen mustards such as cyclophosphamide, alkyl sulfonates, nitrosoureas, ethylenimines, triazenes, folate antagonists, purine analogs, pyrimidine analogs, anthracyclines, bleomycins, mitomycins, dactinomycins, plicamycin, vinca alkaloids, epipodophyllotoxins, taxanes, glucocorticoids, L-asparaginase, estrogens, androgens, progestins, luteinizing hormones, octreotide actetate, hydroxyurea, procarbazine, mitotane, hexamethylmelamine, carboplatin, mitoxantrone, monoclonal antibodies, levamisole, interferons, interleukins, filgrastim and sargramostim. Chemotherapeutic compositions also comprise other members, i.e., other than TRAIL, of the TNF superfamily of compounds.

Radiotherapy protocols Additionally, in several method embodiments of the present invention the Smac peptidomimetic therapy may be used in connection with chemo-radiation or other cancer treatment protocols used to inhibit tumor cell growth.

For example, but not limited to, radiation therapy (or radiotherapy) is the medical use of ionizing radiation as part of cancer treatment to control malignant cells is suitable for use in embodiments of the present invention. Although radiotherapy is often used as part of curative therapy, it is occasionally used as a palliative treatment, where cure is not possible and the aim is for symptomatic relief. Radiotherapy is commonly used for the treatment of tumors. It may be used as the primary therapy. It is also common to combine radiotherapy with surgery and/or chemotherapy. The most common tumors treated with radiotherapy are breast cancer, prostate cancer, rectal cancer, head & neck cancers, gynecological tumors, bladder cancer and lymphoma. Radiation therapy is commonly applied just to the localized area involved with the tumor. Often the radiation fields also include the draining lymph nodes. It is possible but uncommon to give radiotherapy to the whole body, or entire skin surface. Radiation therapy is usually given daily for up to 35-38 fractions (a daily dose is a fraction). These small frequent doses allow healthy cells time to grow back, repairing damage inflicted by the radiation. Three main divisions of radiotherapy are external beam radiotherapy or teletherapy, brachytherapy or sealed source radiotherapy and unsealed source radiotherapy, which are all suitable examples of treatment protocol in the present invention. The differences relate to the position of the radiation source; external is outside the body, while sealed and unsealed source radiotherapy has radioactive material delivered internally. Brachytherapy sealed sources are usually extracted later, while unsealed sources are injected into the body. Administration of the Smac peptidomimetic may occur prior to, concurrently with the treatment protocol. Annexin V/Propidium Iodide Staining—To show the ability of Smac mimetics to induce apoptosis, Annexin V-fluorescein isothiocyanate staining was performed as per manufacturer's protocol (Invitrogen, Carlsbad, Calif.). Briefly, cells were exposed to various concentrations of Smac mimetics for 18-24 hrs. and then removed from the assay plate by trypsinization. Cells were then pelleted and resuspended in assay buffer (supplied by manufacturer), Annexin V and propidium iodide were added to the cell preparations and incubated for 1 hour in the dark at room temperature. Following the incubation additional buffer (200 µl) was then added to each tube, and the samples were analyzed immediately by flow cytometry. In the presence of Smac mimetics apoptosis was strongly promoted, as assessed by annexin/PI staining and analyzed by flow cytometry. The amplification in the number of apoptotic cells (Annexin V positive/propidium iodide negative—lower right quadrant) by IAP antagonists as compared to control was dose dependent and due to the induction of apoptosis and not via increasing the proportion of necrotic cells.

Biological and chemotherapeutics/anti-neoplastic agents and radiation induce apoptosis by activating the extrinsic or intrinsic apoptotic pathways, and, since Smac mimetics relieve inhibitors of apoptotic proteins (IAPs) and, thus, remove the block in apoptosis, the combination of chemotherapeutics/anti-neoplastic agents and radiation with Smac mimetics should work synergistically to facilitate apoptosis.

The relevance of this potent synergy is that it makes possible the use of the Smac peptidomimetics, which are IAP antagonists, to improve the efficacy of the marketed platinum containing compounds (cisplatin and carboplatin). This may be accomplished by lowering the required dose of the poorly tolerated platinum containing compounds and/or by improving the response rate at the marketed dose.

The present invention is not limited to the embodiments described and exemplified above, but is capable of variation and modification within the scope of the appended claims.

What is claimed is:
1. A compound of Formula I:

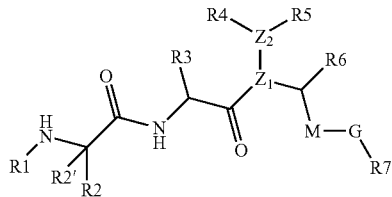

I wherein
$Z_1$ and $Z_2$ are each independently CH or N;
$R_1$ is H or optionally substituted hydroxy, alkyl, cycloalkyl, heterocycloalkyl, aryl, or heteroaryl;
$R_2$ and $R_2'$ are each independently H or optionally substituted alkyl, cycloalkyl, or heterocycloalkyl, or when $R_2'$ is H then $R_2$ and $R_1$ can together form an aziridine or azetidine ring;
$R_3$ and $R_4$ are each independently H or optionally substituted alkyl, cycloalkyl, heterocycloalkyl, aryl, or heteroaryl; or, $R_3$ and $R_4$ are each carbon and are linked by a covalent bond or by an optionally-substituted alkylene or alkenylene group of 1 to 8 carbon atoms where one to three carbon atoms can be replaced by N, O, S(O)$_n$, or C=O;
$R_5$ and $R_6$ are each independently H or optionally substituted hydroxy, alkyl, cycloalkyl, heterocycloalkyl, aryl, or heteroaryl; or $R_5$ and $R_6$ are each carbon and are linked by a covalent bond or by an optionally-substituted alkylene or alkenylene group of 1 to 8 carbon atoms where one to three carbon atoms can be replaced by N, O, S(O)$_n$, or C=O;
M is a bond, optionally substituted alkylene group of 1 to 5 carbon atoms, optionally substituted with a lower alkyl; or M and G together form a bond;
G is a bond, a heteroatom, —S(O)$_n$—, —NR$_8$—, —NCOR$_8$—, or —NS(O)$_n$R$_8$—, where $R_8$ is selected from the group consisting of lower alkyl, optionally-substituted lower alkyl and $C_{3-8}$ cycloalkyl; or M and G together form a bond;
$R_7$ is a cycloalkyl, a heterocycloalkyl, an aryl, or a heteroaryl, each substituted with -L1-$R_{10}$ and each cycloalkyl, heterocycloalkyl, aryl, or heteroaryl is optionally further substituted;
L1 is a covalent bond or $C_{1-6}$ alkylene, alkenylene, or alkynylene;
$R_{10}$ is an optionally substituted 5-, 6-, or 7-membered heterocycloalkyl with at least one N or O atom in the ring or $R_{10}$ is heteroaryl with at least one N atom in the ring;
each n can be the same or different and is 0, 1, or 2;
or a pharmaceutically acceptable salt thereof.

2. The compound of claim 1 or a pharmaceutically acceptable salt thereof wherein when $Z_1$ is N and $Z_2$ is CH, then at least one of the following is true:
(i) $R_5$ and $R_6$ together are not both carbon atoms linked by a single covalent bond;
(ii) $R_5$ and $R_6$ are both carbon atoms linked by a single covalent bond and $R_5$ is disubstituted;
(iii) $R_5$ and $R_6$ are both carbon atoms linked by a single covalent bond and $R_6$ is mono- or disubstituted;
(iv) $R_5$ and $R_6$ are both carbon atoms linked by a single covalent bond and $R_3$ and $R_4$ are both carbon atoms linked by a covalent bond or by an optionally-substituted alkylene or alkenylene group of 1 to 8 carbon atoms where one to three carbon atoms can be replaced by N, O, S(O)$_n$, or C=O.

3. The compound of claim 1 or a pharmaceutically acceptable salt thereof wherein
M is optionally-substituted $C_1$-$C_5$ alkylene, optionally substituted with a lower alkyl;
G is a bond;
$R_7$ is aryl or heteroaryl, each substituted with -L1-R10 and each aryl or heteroaryl is optionally further substituted;
$L_1$ is a covalent bond or $C_1$-$C_4$ alkylene, alkenylene, or alkynylene;
$R_{10}$ is a tetrahydrofuranyl or tetrahydropyranyl moiety each of which is optionally substituted with hydroxy, lower alkyl, lower alkoxy, or optionally-substituted lower alkoxy selected from the group consisting of arylalkyloxy, alkylcarbonyloxy, arylcarbonyloxy, and acetyloxy; or, $R_{10}$ is an optionally-substituted nitrogen-containing 5- to 7-membered heteroaryl or heterocycloalkyl group and (i) R3 and R4 are covalently linked, (ii) R5 and R6 are covalently linked or (iii) both R3 and R4 are covalently linked, and R5 and R6 are covalently linked.

4. The compound of claim 3 or a pharmaceutically acceptable salt thereof wherein
M is $C_1$-$C_3$ alkylene, but not alkenylene or alkynylene, optionally-substituted with lower alkyl;
$L_1$ is a single covalent bond;
$R_{10}$ is tetrahydrofuranyl or tetrahydropyranyl substituted with at least one hydroxy or acetyloxy group.

5. The compound of claim 3 or a pharmaceutically acceptable salt thereof wherein
M is $C_1$-$C_3$ alkylene, but not alkenylene or alkynylene, optionally-substituted with lower alkyl;
$L_1$ is a single covalent bond;
$R_{10}$ is a 5- to 7-membered heteroaryl or heterocycloalkyl group having a single nitrogen atom in the ring and no additional heteroatoms.

6. The compound of claim 1 or a pharmaceutically acceptable salt thereof wherein $R_1$ is H, methyl, allyl, propargyl, ethyl, cycloalkyl, hydroxyethyl or cyclo alkylmethyl.

7. The compound of claim 1 or a pharmaceutically acceptable salt thereof wherein $R_2$ and $R_2$' are independently H, methyl, fluoromethyl, difluoromethyl, ethyl, hydroxyethyl, fluoroethyl, and cycloalkyl.

8. The compound of claim 1 or a pharmaceutically acceptable salt thereof wherein $R_3$ and $R_4$ are independently H, methyl, ethyl, isopropyl, isobutyl, sec-butyl, tert-butyl, cycloalkyl, heterocycloalkyl, aryl, or heteroaryl, optionally-substituted with hydroxyl, mercapto, sulfonyl, alkylsulfonyl, halogen, pseudohalogen, amino, carboxyl, alkyl, haloalky, pseudohaloalkyl, alkoxy, or alkylthio, or $R_3$ and $R_4$ are carbon atoms and are linked by a covalent bond or by an optionally-substituted alkylene or alkenylene group of 1 to 3 carbon atoms of which 1 or more atoms can be replaced by N, O, $S(O)_n$, or C=O.

9. The compound of claim 1 or a pharmaceutically acceptable salt thereof wherein $R_5$ and $R_6$ are independently optionally substituted lower alkyl or $C_3$-$C_8$ cycloalkyl wherein the optional substituents are hydroxy or lower alkoxy, or $R_5$ and $R_6$ are carbon atoms and are linked by a covalent bond or by an optionally-substituted alkylene or alkenylene group of 1 to 3 carbon atoms of which 1 or more atoms can be replaced by N, O, $S(O)_n$, or C=O.

10. The compound of claim 1 or a pharmaceutically acceptable salt thereof wherein
$R_1$ is H, methyl, allyl, propargyl, ethyl, cycloalkyl, hydroxyethyl or cycloalkylmethyl;
$R_2$ and $R_2$' are independently H, methyl, fluoromethyl, difluoromethyl, ethyl, hydroxyethyl, fluoroethyl, and cycloalkyl;
$R_3$ and $R_4$ are independently optionally substituted lower alkyl or $C_3$-$C_8$ cycloalkyl wherein the optional substituents are hydroxy or lower alkoxy, or $R_3$ and $R_4$ are carbon atoms and are linked by a covalent bond or by an optionally-substituted alkylene or alkenylene group of 1 to 3 carbon atoms of which 1 or more atoms can be replaced by N, O, $S(O)_n$, or C=O;
$R_5$ and $R_6$ are independently optionally substituted lower alkyl or $C_3$-$C_8$ cycloalkyl wherein the optional substituents are hydroxy or lower alkoxy, or $R_5$ and $R_6$ are carbon atoms and are linked by a covalent bond or by an optionally-substituted alkylene or alkenylene group of 1 to 3 carbon atoms of which 1 or more atoms can be replaced by N, O, $S(O)_n$, or C=O;
M is $C_1$-$C_3$ alkylene optionally-substituted with lower alkyl.

11. The compound of claim 1 or a pharmaceutically acceptable salt thereof wherein
$R_1$ is H, methyl, allyl, propargyl, ethyl, cycloalkyl, hydroxyethyl or cycloalkylmethyl;
$R_2$ and $R_2$' are independently H, methyl, fluoromethyl, difluoromethyl, ethyl, hydroxyethyl, fluoroethyl, and cycloalkyl;
$R_3$ and $R_4$ are linked by a covalent bond or by an optionally-substituted alkylene or alkenylene group of 1 to 3 carbon atoms of which 1 or more atoms can be replaced by N, O, $S(O)_n$, or C=O;
$R_5$ and $R_6$ are independently H or optionally substituted lower alkyl or $C_3$-$C_8$ cycloalkyl wherein the optional substituents are hydroxy or lower alkoxy, or $R_5$ and $R_6$ are carbon atoms and are linked by a covalent bond or by an optionally-substituted alkylene or alkenylene group of 1 to 8 carbon atoms where one to three carbon atoms can be replaced by N, O, $S(O)_n$, or C=O;
M is $C_1$-$C_3$ alkylene optionally-substituted with lower alkyl.

12. The compound of claim 1 or a pharmaceutically acceptable salt thereof wherein
$R_7$ is IIa or IIb:

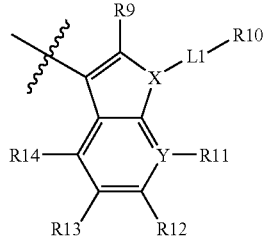

(IIa)

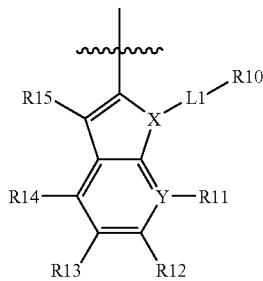

(IIb)

$L_1$ is a single covalent bond
X is —N—, —C=C($R_{16}$)—, —N=C— or —C(O)N—;
Y is —C—, —N—, or —$N^+$—; such that,
When Y is —C— then $R_9$, $R_{11}$, $R_{12}$, $R_{13}$, $R_{14}$, $R_{15}$, and $R_{16}$ are, independently, —H, halogen, or optionally substituted alkyl, cycloalkyl, aryl, heteroaryl, hydroxy, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime; provided that when X is —N— or —C(O)—N—, -$L_1$-$R_{10}$ is bound to the —N— atom; and, when X is —C=C($R_{16}$)— or —N=C—, -$L_1$-$R_{10}$ is bound to the —C= atom; and
When Y is —N— or —$N^+$—, then $R_{11}$ is absent or —$O^-$, and $R_9$, $R_{12}$, $R_{13}$, $R_{14}$, $R_{15}$, and $R_{16}$ are, independently, —H, halogen, or optionally substituted alkyl, cycloalkyl, heterocycloalkyl, aryl, heteroaryl, hydroxyl, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime; provided that when X is —N— or —C(O)—N—, -L$_1$-R$_{10}$ is bound to the —N— atom; and, when X is —C=C(R$_{16}$)— or —N=C—, -L$_1$-R$_{10}$ is bound to the —C= atom.

13. The compound of claim 1 or a pharmaceutically acceptable salt thereof having the formula (III):

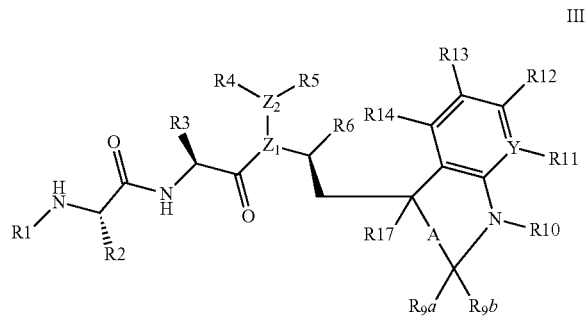

III wherein
Y is —C—, —N—, or —N$^+$—; such that,
A is a single or double bond;
When A is a single bond and Y is —C— then R$_9$a, R$_9$b, R$_{11}$, R$_{12}$, R$_{13}$, R$_{14}$, and R$_{17}$ are, independently, —H, halogen, or optionally substituted alkyl, cycloalkyl, heterocycloalkyl, aryl, heteroaryl, hydroxy, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime;
When A is a single bond and Y is —N— or —N$^+$—, then R$_{11}$ is absent or —O$^-$, and R$_9$a, R$_9$b, R$_{12}$, R$_{13}$, R$_{14}$, and R$_{17}$ are, independently, —H, halogen, or optionally substituted alkyl, cycloalkyl, heterocycloalkyl, aryl, heteroaryl, hydroxy, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime;
When A is a double bond and Y is —C— then R$_9$b and R$_{17}$ are absent; and R$_9$a, R$_{11}$, R$_{12}$, R$_{13}$, and R$_{14}$ are, independently, —H, halogen, or optionally substituted alkyl, cycloalkyl, heterocycloalkyl, aryl, heteroaryl, hydroxy, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime;
When A is a double bond and Y is —N— or —N$^+$—, then R$_9$b and R$_{17}$ are absent; and R$_{11}$ is absent or —O$^-$, and R$_9$a, R$_{12}$, R$_{13}$, and R$_{14}$ are, independently, —H, halogen, or optionally substituted alkyl, cycloalkyl, heterocycloalkyl, aryl, heteroaryl, hydroxyl, alkoxy, polyalkylether, amino, alkylamino, dialkylamino, alkoxyalkyl, sulfonate, aryloxy, heteroaryloxy, acyl, acetyl, or carboxylate, sulfonate, sulfone, imine, or oxime.

14. The compound of claim 12 or a pharmaceutically acceptable salt thereof wherein
R$_7$ is IIa or IIb;
X is —N—;
Y is —C—, —N—, or —N$^+$—; such that When Y is —C—, then R$_9$, R$_{11}$, R$_{12}$, R$_{13}$, R$_{14}$ and R$_{15}$ are, independently, —H, halogen, or optionally substituted alkyl, cycloalkyl, heterocycloalkyl, aryl, heteroaryl, hydroxyl, alkoxy, polyalkylether, amino, alkylamino, dialkylamino, alkoxyalkyl, sulfonate, aryloxy or heteroaryloxy;
When Y is —N—, then R$_{11}$ is absent, and R$_9$, R$_{12}$, R$_{13}$, R$_{14}$ and R$_{15}$ are, independently, —H, halogen, or optionally substituted alkyl, cycloalkyl, heterocycloalkyl, aryl, heteroaryl, hydroxyl, alkoxy, polyalkylether, amino, alkylamino, dialkylamino, alkoxyalkyl, sulfonate, aryloxy or heteroaryloxy;
When Y is —N$^+$—, then R$_{11}$ is —O$^-$, and R$_9$, R$_{12}$, R$_{13}$, R$_{14}$ and R$_{15}$ are, independently, —H, halogen, or optionally substituted alkyl, cycloalkyl, heterocycloalkyl, aryl, heteroaryl, hydroxyl, alkoxy, polyalkylether, amino, alkylamino, dialkylamino, alkoxyalkyl, sulfonate, aryloxy or heteroaryloxy;
R$_3$ is methyl, ethyl, isopropyl, isobutyl, sec-butyl, tert-butyl, cycloalkyl, heterocycloalkyl, aryl, or heteroaryl, optionally-substituted with hydroxyl, mercapto, halogen, pseudohalogen, amino, carboxyl, alkyl, haloalkyl, pseudohaloalkyl, alkoxy, or alkylthio;
R$_2$ is —H, methyl, fluoromethyl, difluoromethyl, ethyl, fluoroethyl, and cycloalkyl;
R$_2$' is H;
R$_1$ is selected from H, methyl, allyl, propargyl, ethyl, cycloalkyl, or cycloalkylmethyl;
Z$_1$ is nitrogen;
Z$_2$ is —CH—;
R$_4$ is —H and R$_5$ and R$_6$ are both carbon atoms and together form C$_2$-C$_4$ alkylene; or, R$_3$ and R$_4$ are both carbon atoms and together form C$_2$-C$_4$ alkylene; or, both R$_5$ and R$_6$ together and R$_3$ and R$_4$ together both form C$_2$-C$_4$ alkylene groups;
L$_1$ is a covalent bond.

15. The compound of claim 14 or a pharmaceutically acceptable salt thereof wherein
R$_9$, R$_{11}$, R$_{12}$, R$_{13}$, R$_{14}$ and R$_{15}$ are, independently, —H, -halogen, or optionally-substituted lower alkyl;
R$_3$ is optionally-substituted lower alkyl, C$_3$-C$_8$ cycloalkyl, or heterocycloalkyl wherein the optional substituents are hydroxy, lower alkoxy, or lower alkyl;
R$_2$ is optionally-substituted lower alkyl, C$_3$-C$_8$ cycloalkyl, or heterocycloalkyl wherein the optional substituents are hydroxy, lower alkoxy, or lower alkyl;
R$_2$' is H;
R$_1$ is —H or lower alkyl;
R$_5$ and R$_6$ are both carbon atoms and are linked by a covalent bond;
R$_4$ is —H;
Z$_2$ is —CH—;
R$_{10}$ is tetrahydropyran, tetrahydrofuran, D- or L-fucose, D- or L-xylose, D- or L-galactose, or D- or L-glucose, pyrrolidine, piperidine, perhydroazapine, pyridine, pyrimidine, or pyrazine.

16. The compound of claim 1 selected from the group consisting of Compounds A through U and Compounds HH through SS, as follows, or a pharmaceutically acceptable salt thereof:

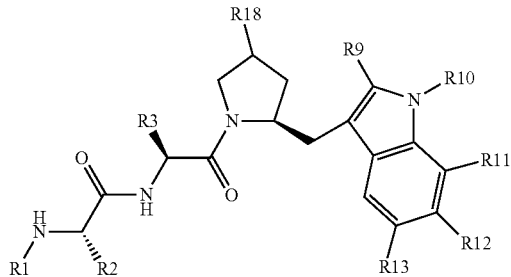

| Compound | R1 | R2 | R3 | R18 | R9 | R13 | R12 | R11 | R10 |
|---|---|---|---|---|---|---|---|---|---|
| A | Me | Me | tBu | H | 4-F-phenyl | H | F | H | D-xylose |
| B | Me | Me | iPr | H | 4-F-phenyl | H | F | H | D-xylose |
| C | Me | Me | tBu | H | 4-F-phenyl | H | F | Me | L-fucose |
| D | Me | Me | iPr | H | H | H | H | Me | L-fucose |
| E | Me | Me | iPr | H | H | H | H | H | D-xylose |
| F | Me | Me | tBu | H | H | H | F | H | L-fucose |
| G | Me | Me | cHex | H | H | H | F | H | L-fucose |
| H | Me | Me | iPr | H | H | H | F | H | L-fucose |
| I | Me | Me | iPr | H | H | H | F | H | D-xylose |
| J | Me | Me | iPr | H | H | H | F | H | D-glucose |
| K | Me | Me | iPr | H | H | H | F | H | D-galactose |
| L | Me | Me | iPr | H | H | H | F | H | D-galactose tetra acetate |
| M | Me | Me | cHex | H | H | H | F | H | D-xylose |
| N | Me | Me | tBu | H | H | H | F | H | D-xylose |
| O | Me | Me | R-(Me)CHOMe | H | 4-F-phenyl | H | F | H | L-fucose |
| P | Me | Me | R-(Me)CHOMe | S-OH | 4-F-phenyl | Me | H | H | L-fucose |
| Q | Me | Me | tert-Butyl | S-OH | 4-F-phenyl | Me | H | H | L-fucose |
| R | Me | Me | R-(Me)CHOMe | H | 4-F-phenyl | Me | H | H | L-fucose |
| S | Me | Me | tert-Butyl | H | 4-F-phenyl | Me | H | H | L-fucose |
| T | Me | Me | tert-Butyl | S-OH | 4-F-phenyl | H | F | H | L-fucose |
| U | Me | Me | R-(Me)CHOMe | S-OH | 4-F-phenyl | H | F | H | L-fucose |

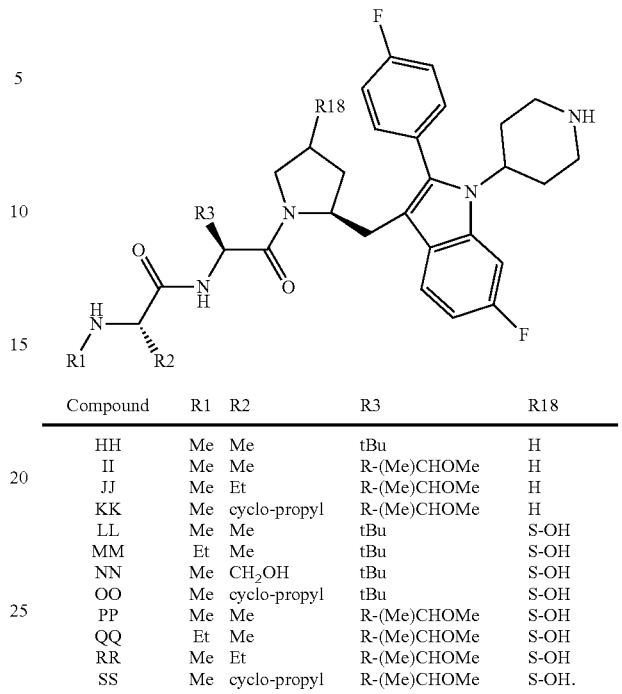

| Compound | R1 | R2 | R3 | R18 |
|---|---|---|---|---|
| HH | Me | Me | tBu | H |
| II | Me | Me | R-(Me)CHOMe | H |
| JJ | Me | Et | R-(Me)CHOMe | H |
| KK | Me | cyclo-propyl | R-(Me)CHOMe | H |
| LL | Me | Me | tBu | S-OH |
| MM | Et | Me | tBu | S-OH |
| NN | Me | CH$_2$OH | tBu | S-OH |
| OO | Me | cyclo-propyl | tBu | S-OH |
| PP | Me | Me | R-(Me)CHOMe | S-OH |
| QQ | Et | Me | R-(Me)CHOMe | S-OH |
| RR | Me | Et | R-(Me)CHOMe | S-OH |
| SS | Me | cyclo-propyl | R-(Me)CHOMe | S-OH. |

17. A compound having Formula IV, or a pharmaceutically acceptable salt thereof:

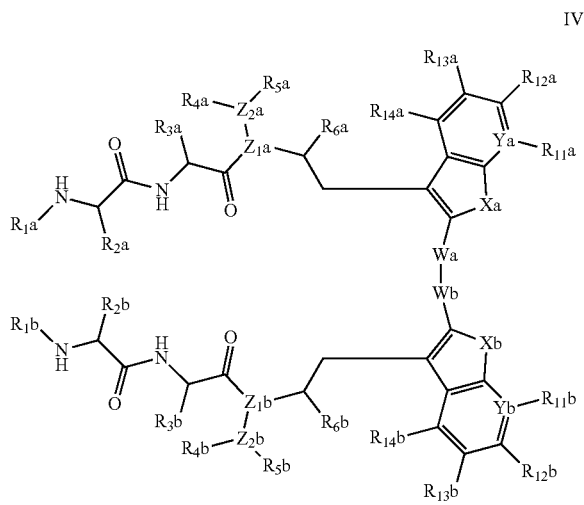

IV wherein $Z_1a$, $Z_2a$, $Z_1b$, and $Z_2b$ are independently CH or N;

$R_1a$ and $R_1b$ are independently H or optionally substituted hydroxyl, alkyl, cycloalkyl, heterocycloalkyl, aryl, or heteroaryl; and when $R_2a'$ is H then $R_2a$ and $R_1a$ can together form an aziridine or azetidine ring and when $R_2b'$ is H then $R_2b$ and $R_1b$ can together form an aziridine or azetidine ring;

$R_2a$, and $R_2b$ are independently H or optionally substituted alkyl, cycloalkyl, or heterocycloalkyl; or when $R_2a'$ is H then $R_2a$ and $R_1a$ can together form an aziridine or azetidine ring and when $R_2b'$ is H then $R_2b$ and $R_1b$ can together form an aziridine or azetidine ring;

$R_3a$, $R_3b$, $R_4a$ and $R_4b$ are independently H or optionally substituted alkyl, cycloalkyl, heterocycloalkyl, aryl, or heteroaryl; or, $R_4a$ and $R_3a$, or $R_4b$ and $R_3b$, or both, are carbon atoms linked by an optionally-substituted alkylene or alkenylene group of 1 to 8 carbon atoms where one to three carbon atoms can be replaced by N, O, $S(O)_n$, or C=O;

$R_5a$, $R_6a$, $R_5b$, and $R_6b$ are independently H or optionally substituted hydroxyl, alkyl, cycloalkyl, heterocycloalkyl, aryl, or heteroaryl; or $R_5a$ and $R_6a$ or $R_5b$ and $R_6b$, or both, are carbon atoms linked by an optionally-substituted alkylene or alkenylene group of 1 to 8 carbon atoms where one to three carbon atoms can be replaced by N, O, $S(O)_n$, or C=O;

n can be the same or different in each usage and is 0, 1, or 2;

Xa is —O—, —N(La—$R_{10}$a)—, —S—, optionally-substituted —C(La—$R_{10}$a)=CH—, —C(O)—O—, —C(O)—N(La—$R_{10}$a)—, —N=C(La—$R_{10}$a)-;

Xb is —O—, —N(Lb-$R_{10}$b)—, —S—, optionally-substituted —C(Lb-$R_{10}$b)=CH—, —C(O)—O—, —C(O)—N(Lb-$R_{10}$b)—, —N=C(Lb-$R_{10}$b)-, provided that if Xb is —O—, —S—, or —C(O)—O—, then Xa is —N(La—$R_{10}$a)—, optionally-substituted —C(La—$R_{10}$a)=CH—, —C(O)—N(La—$R_{10}$a)—, or —N=C(La—$R_{10}$a)-, and if Xa is —O—, —S—, or —C(O)—O—, then Xb is —N(Lb-$R_{10}$b)—, optionally-substituted —C(Lb-$R_{10}$b)=CH—, —C(O)—N(Lb-$R_{10}$b)—, or —N=C(Lb-$R_{10}$b)-;

La and Lb are independently a covalent bond or $C_1$-$C_4$ alkylene, alkenylene, or alkynylene;

$R_{10}a$ and $R_{10}b$ are independently an optionally substituted 5-, 6-, or 7-membered heterocycloalkyl with at least one N or O atom in the ring or heteroaryl with at least one N atom in the ring provided that one but not both of $R_{10}a$ and $R_{10}b$ can be —H or absent;

Wa and Wb are together a Linker and

Ya and Yb are independently —C—, —N—, or —N+—; such that, (a) when Ya or Yb is —C— then $R_{11}a$, $R_{11}b$, $R_{12}a$, $R_{12}b$, $R_{13}a$, $R_{13}b$, $R_{14}a$ and $R_{14}b$ respectively are independently —H, halogen, or optionally substituted alkyl, cycloalkyl, heterocycloalkyl, aryl, heteroaryl, hydroxy, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime;

(b) when Ya or Yb is —N— then $R_{11}a$, and $R_{11}b$ respectively are absent, and $R_{12}a$, $R_{12}b$, $R_{13}a$, $R_{13}b$, $R_{14}a$ and $R_{14}b$ respectively are independently —H, halogen, or optionally substituted alkyl, cycloalkyl, heterocycloalkyl, aryl, heteroaryl, hydroxy, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime and (c) when Ya or Yb is —N+—, then $R_{11}a$ and $R_{11}b$ respectively are —O⁻ and $R_{12}a$, $R_{12}b$, $R_{13}a$, $R_{13}b$, $R_{14}a$, and $R_{14}b$ are, independently, —H, halogen, or optionally substituted alkyl, cycloalkyl, heterocycloalkyl, aryl, heteroaryl, hydroxy, alkoxy, polyalkylether, amino, alkylamino, dialkylamino, alkoxyalkyl, sulfonate, aryloxy, heteroaryloxy, acyl, acetyl, carboxylate, sulfonate, sulfone, imine, or oxime.

18. The compound of claim 17 or a pharmaceutically acceptable salt thereof wherein when $Z_1a$ is N and $Z_2a$ is CH, and $Z_1b$ is N and $Z_2b$ is CH, then at least one of the following is true:

(i) $R_5a$ and $R_6a$ are not both carbon atoms linked by a single covalent bond;

(ii) $R_5a$ and $R_6a$ are both carbon atoms linked by a single covalent bond and $R_6a$ is disubstituted;

(iii) $R_5a$ and $R_6a$ are both carbon atoms linked by a single covalent bond and $R_6a$ is mono- or disubstituted;

(iv) $R_5a$ and $R_6a$ are both carbon atoms linked by a single covalent bond and $R_3a$ and $R_4a$ are both carbon atoms linked by a covalent bond or by an optionally-substituted alkylene or alkenylene group of 1 to 8 carbon atoms where one to three carbon atoms can be replaced by N, O, $S(O)_n$, or C=O;

(v) $R_5a$ and $R_6a$ are both carbon atoms linked by a single covalent bond and R2a is not H.

19. The compound of claim 17 or a pharmaceutically acceptable salt thereof wherein $R_3a$, $R_4a$, $R_3b$, and $R_4b$ are independently selected from H, methyl, ethyl, isopropyl, isobutyl, sec-butyl, tert-butyl, cycloalkyl, heterocycloalkyl, aryl, or heteroaryl, optionally-substituted with hydroxyl, mercapto, sulfonyl, alkylsulfonyl, halogen, pseudohalogen, amino, carboxyl, alkyl, haloalky, pseudohaloalkyl, alkoxy, or alkylthio.

20. The compound of claim 17 or a pharmaceutically acceptable salt thereof wherein $R_2a$ and $R_2b$ are independently selected from —H, methyl, fluoromethyl, difluoromethyl, ethyl, fluoroethyl, hydroxyethyl, and cycloalkyl.

21. The compound of claim 17 or a pharmaceutically acceptable salt thereof wherein $R_1a$ and $R_1b$ are independently selected from H, methyl, allyl, propargyl, ethyl, hydroxyethyl, cycloalkyl, or cycloalkylmethyl.

22. The compound of claim 17 or a pharmaceutically acceptable salt thereof wherein $R_3a$, $R_4a$, $R_3b$, and $R_4b$ are independently optionally substituted lower alkyl or $C_3$-$C_8$ cycloalkyl wherein the optional substituents are hydroxy or lower alkoxy.

23. The compound of claim 17 or a pharmaceutically acceptable salt thereof wherein $Z_1a$ and $Z_1b$ are both N and $Z_2a$ and $Z_2b$ are both C and wherein $R_5a$ and $R_6a$, and $R_5b$ and $R_6b$, are each carbon and are linked by a covalent bond or by an optionally-substituted alkylene or alkenylene group of 1 to 8 carbon atoms where one to three carbon atoms can be replaced by N, O, $S(O)_n$, or C=O.

24. The compound of claim 17 or a pharmaceutically acceptable salt thereof wherein $Z_1a$ and $Z_1b$ are both N and $Z_2a$ and $Z_2b$ are both C and wherein $R_3a$ and $R_4a$, and $R_3b$ and $R_4b$, are each carbon and are linked by a covalent bond or by an optionally-substituted alkylene or alkenylene group of 1 to 8 carbon atoms where one to three carbon atoms can be replaced by N, O, $S(O)_n$, or C=O.

25. The compound of claim 17 or a pharmaceutically acceptable salt thereof wherein Wa and Wb together are a covalent bond or optionally substituted alkylene, cycloalkyl, or aryl, of 2 to 20 carbon atoms where one or more carbon atoms can be replaced with N, O, or $S(O)_n$; and Xa and Xb are independently —O—, —S—, or —C(O)—O—.

26. The compound of claim 17 or a pharmaceutically acceptable salt thereof wherein one of $R_{10}a$ and $R_{10}b$ is —H or is absent.

27. A compound selected from the group consisting of Compounds V through Z and AA through GG, as follows, or a pharmaceutically acceptable salt thereof:

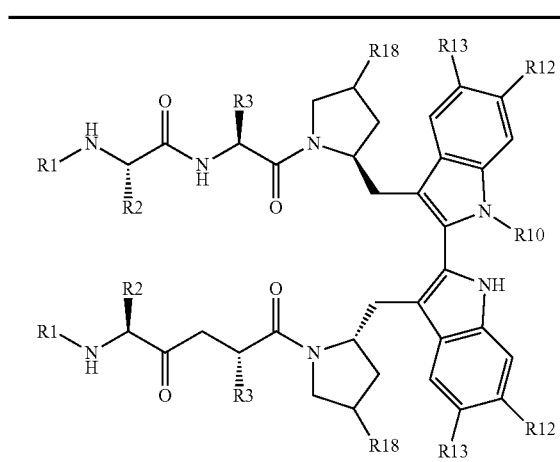

| Compound | R1 | R2 | R3 | R18 | R13 | R12 | R10 |
|---|---|---|---|---|---|---|---|
| V | Me | Me | iPr | H | H | F | L-fucose |
| W | H | H | iPr | H | H | F | L-fucose |
| X | H | H | iPr | H | H | F | D-xylose |
| Y | Me | Me | iPr | H | H | F | D-xylose |
| Z | Me | Me | R-(Me)CHOMe | H | F | H | D-galactose |
| AA | Me | Me | iPr | H | F | H | D-galactose |
| BB | Me | Me | R-(Me)CHOMe | H | F | H | D-glucose |
| CC | Me | Me | iPr | H | F | H | D-glucose |
| DD | Me | Me | iPr | H | F | H | L-fucose |
| EE | Me | Me | R-(Me)CHOMe | H | H | F | L-fucose |
| FF | Me | Me | R-(Me)CHOMe | S-OH | H | F | L-fucose |
| GG | Me | Me | R-(Me)CHOMe | S-OH | H | F | L-fucose. |

28. The compound of claim 1 or a pharmaceutically acceptable salt thereof having the formula

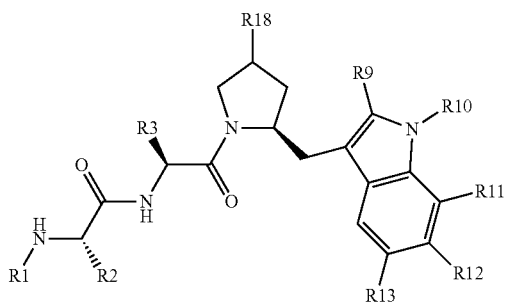

wherein $R_1$, $R_2$, and $R_3$ are independently lower alkyl, lower alkoxy, lower alkanol, or $C_3$-$C_6$ cycloalkyl; $R_{18}$ is H or OH; $R_9$ is H or phenyl optionally substituted with halogen; $R_{11}$, $R_{12}$, and $R_{13}$ are independently H or halogen and $R_{10}$ is an optionally substituted 5-, 6-, or 7-membered heterocycloalkyl with at least one N or O atom in the ring or $R_{10}$ is heteroaryl with at least one N atom in the ring.

29. The compound of claim 17 or a pharmaceutically acceptable salt thereof having the formula

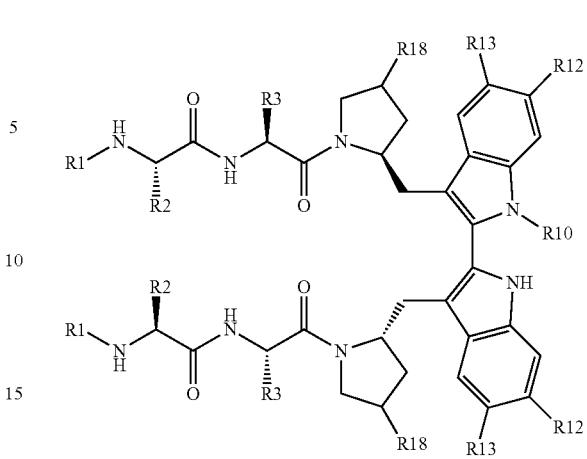

wherein $R_1$, $R_2$, and $R_3$ are independently lower alkyl, lower alkoxy, lower alkanol, or $C_3$-$C_6$ cycloalkyl; $R_{18}$ is H or OH; $R_{11}$, $R_{12}$, and $R_{13}$ are independently H or halogen and $R_{10}$ is an optionally substituted 5-, 6-, or 7-membered heterocycloalkyl with at least one N or O atom in the ring or $R_{10}$ is heteroaryl with at least one N atom in the ring.

30. A method for inducing apoptosis in a cell comprising contacting the cell with a compound of claim 1 in an amount sufficient to induce apoptosis in the cell.

31. The method of claim 30, wherein said cell is neoplastic.

32. The method of claim 30, wherein said cell overexpresses an inhibitor of caspase.

33. The method of claim 32, wherein the inhibitor inhibits activation or activity of one or more of a caspase selected from caspase-3, caspase-7 and caspase-9.

34. A method of stimulating apoptosis in a cell comprising contacting the cell with a compound of claim 1 in an amount sufficient to stimulate apoptosis in the cell.

35. The method of claim 34, wherein said cell is a cancer cell.

36. A method of enhancing apoptosis of pathogenic cells in vivo in an individual comprising administering to the individual a therapeutically effective amount of a compound of claim 1.

37. The method of claim 36 further comprising administering a second therapy selected from radiation, chemotherapy, immunotherapy, photodynamic therapy and combinations thereof.

38. A pharmaceutical composition comprising: a compound selected from a compound of claim 1 and a pharmaceutically acceptable excipient.

39. The composition of claim 38 further comprising a second chemotherapeutic agent.

40. The composition of claim 39, wherein said second chemotherapeutic agent is selected from altretamine, busulfan, carboplatin, carmustine, chlorambucil, cisplatin, cyclophosphomide, dacarbazine, hexamethylmelamine, ifosfamide, lomustine, melphalan, mechlorethamine, oxaliplatin, procarbazine, streptozocin, temozolomide, thiotepa, uramustine, docetaxel, etoposide, irinotecan, paclitaxel, tenisopide, topotecan, vincristine, vinblastine, vindesine, vinorelbine, bleomycin, dactinomycin, daunorubicin, epirubicin, hydroxyurea, idarubicin, mitomycin, mitoxantrone, plicamycin, azathioprine, capecitabine, cladribine, cytarabine, fludarabine, fluorouracil, floxuridine, gemcitabine, mercaptopurine, methotrexate, nelarabine, pemeterxed, pentostatin, thioguanine, camptothecin, irinotecan, topotecan, BNP 1350, SN 38, 9-amino-camptothecan, lurtotecan, gimatecan, diflomotecan, an anthracycline, anthraquinone, podophyllotoxin, doxorubicin, epirubicin, idarubicin, nemorubicin, mitoxantrone, loxoxantrone, etoposide, teniposide and combinations thereof.

41. The composition of claim 39, wherein said second chemotherapeutic agent is selected from alkylating agents, plant alkaloids, antitumor antibiotics, antimetabolites, topoisomerase inhibitors and combinations thereof.

42. The compound of claim 3 or a pharmaceutically acceptable salt thereof wherein
- $R_1$ is H, methyl, allyl, propargyl, ethyl, cycloalkyl, hydroxyethyl or cycloalkylmethyl;
- $R_2$ and $R_2'$ are independently H, methyl, fluoromethyl, difluoromethyl, ethyl, hydroxyethyl, fluoroethyl, and cycloalkyl;
- $R_3$ and $R_4$ are independently optionally substituted lower alkyl or $C_3$-$C_8$ cycloalkyl wherein the optional substituents are hydroxy or lower alkoxy, or $R_3$ and $R_4$ are carbon atoms and are linked by a covalent bond or by an optionally-substituted alkylene or alkenylene group of 1 to 3 carbon atoms of which 1 or more atoms can be replaced by N, O, $S(O)_n$, or C=O;
- $R_5$ and $R_6$ are independently optionally substituted lower alkyl or $C_3$-$C_8$ cycloalkyl wherein the optional substituents are hydroxy or lower alkoxy, or $R_5$ and $R_6$ are carbon atoms and are linked by a covalent bond or by an optionally-substituted alkylene or alkenylene group of 1 to 3 carbon atoms of which 1 or more atoms can be replaced by N, O, $S(O)_n$, or C=O;
- M is $C_1$-$C_3$ alkylene optionally-substituted with lower alkyl.

* * * * *

UNITED STATES PATENT AND TRADEMARK OFFICE
CERTIFICATE OF CORRECTION

PATENT NO. : 8,143,426 B2
APPLICATION NO. : 11/782315
DATED : March 27, 2012
INVENTOR(S) : Stephen M. Condon et al.

It is certified that error appears in the above-identified patent and that said Letters Patent is hereby corrected as shown below:

Column 62, Claim 18, Line 8:

Delete "and $R_6a$ is disubstituted" and insert -- and $R_5a$ is disubstituted --

Signed and Sealed this
Eighteenth Day of December, 2012

David J. Kappos
*Director of the United States Patent and Trademark Office*